US010988737B2

(12) United States Patent
Baumert et al.

(10) Patent No.: US 10,988,737 B2
(45) Date of Patent: Apr. 27, 2021

(54) CLINICAL GENE SIGNATURE-BASED HUMAN CELL CULTURE MODEL AND USES THEREOF

(71) Applicants: UNIVERSITE DE STRASBOURG, Strasbourg (FR); INSERM (INSTITUT NATIONAL DE LA SANTE ET DE LA RECHERCHE MEDICALE), Paris (FR); INSTITUT HOSPITALIER UNIVERSITAIRE DE STRASBOURG, Strasbourg (FR); ICAHN SCHOOL OF MEDICINE AT MOUNT SINAI, New York, NY (US)

(72) Inventors: Thomas Baumert, Freiburg (DE); Yujin Hoshida, Englewood Cliffs, NJ (US)

(73) Assignees: Universite de Strasbourg, Strasbourg (FR); Institut National de la Sante et de la Recherche Medicale Institut, Paris (FR); Hospitalier Universitaire de Strasbourg, Strasbourg (FR); ICAHN School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 15/568,959

(22) PCT Filed: Apr. 28, 2016

(86) PCT No.: PCT/EP2016/059477
§ 371 (c)(1),
(2) Date: Oct. 24, 2017

(87) PCT Pub. No.: WO2016/174130
PCT Pub. Date: Nov. 3, 2016

(65) Prior Publication Data
US 2018/0119096 A1 May 3, 2018

Related U.S. Application Data

(60) Provisional application No. 62/153,727, filed on Apr. 28, 2015.

(51) Int. Cl.
C12N 5/071 (2010.01)
C12N 5/09 (2010.01)
G01N 33/50 (2006.01)
G01N 33/574 (2006.01)
A61K 31/00 (2006.01)
A61P 1/16 (2006.01)

(52) U.S. Cl.
CPC .............. C12N 5/067 (2013.01); A61K 31/00 (2013.01); A61P 1/16 (2018.01); C12N 5/0693 (2013.01); G01N 33/5067 (2013.01); G01N 33/57438 (2013.01); C12N 2500/62 (2013.01); C12N 2502/1157 (2013.01); C12N 2502/14 (2013.01); C12N 2503/02 (2013.01); C12N 2506/30 (2013.01); G01N 2800/085 (2013.01)

(58) Field of Classification Search
None
See application file for complete search history.

(56) References Cited

U.S. PATENT DOCUMENTS

| | | |
|---|---|---|
| 2002/0142449 A1 | 10/2002 | Kwong et al. |
| 2014/0086939 A1 | 3/2014 | Karin et al. |
| 2015/0184124 A1 | 7/2015 | Tyrrell et al. |

FOREIGN PATENT DOCUMENTS

WO 2014/033546 3/2014

OTHER PUBLICATIONS

Schrader et al. Co-Culture of Hepatoma Cells With Hepatic Stellate Cells Promotes Tumour Cell Proliferation and Survival; Journal of Hepatology, vol. 50, Supplement 1, p. S200 (Year: 2009).*
Jammart et al. Very-Low-Density Lipoprotein (VLDL)-Producing and Hepatitis C Virus-Replicating HEP2G Cells Secrete No More Lipoviroparticles Than VLDL-Deficient HUH7.5 Cells; Journal of Virology, vol. 87, No. 9, pp. 5065-5080. (Year: 2013).*
Hoshida et al. Gene Expression in Fixed Tissues and Outcome in Hepatocellular Carcinoma; The New England Journal of Medicine, vol. 359, No. 19, pp. 1995-2004 (Year: 2008).*
Yu et al. Identification of Hepatitis C Virus Inhibitors Targeting Different Aspects of Infection Using a Cell-Based Assay; Antimicrobial Agents and Chemotherapy, vol. 56, No. 12, pp. 6109-6120. (Year: 2012).*

(Continued)

*Primary Examiner* — Antonio Galisteo Gonzalez
(74) *Attorney, Agent, or Firm* — Morgan, Lewis & Bockius LLP

(57) ABSTRACT

The present invention provides a simple and robust human liver cell-based system in which persistent hepatitis C infection, persistent hepatitis B infection or ethanol exposure induces a clinical Prognostic Liver Signature (PLS) high-risk gene signature. The cellular model system for hepatocellular carcinoma (HCC)/cirrhosis development and progression may be used in the screening of compounds useful in the treatment and/or prevention of cirrhosis and/or HCC as well as in the identification biomarkers for the prediction of liver disease (especially cirrhosis) progression and HCC. The present invention also relates to specific compounds that have been identified, using such screening methods, as useful in the treatment and/or the prevention of HCC/cirrhosis.

15 Claims, 11 Drawing Sheets

(56) References Cited

OTHER PUBLICATIONS

International Search Report and Written Opinion of the International Searching Authority dated Sep. 26, 2016, which issued during prosecution of International Application No. PCT/EP2016/059477.

* cited by examiner

CLINICAL GENE SIGNATURE-BASED HUMAN CELL CULTURE MODEL AND USES THEREOF

RELATED PATENT APPLICATIONS

The present patent application is filed pursuant to 35 U.S.C. § 371 as a U.S. National Phase Application of International Patent Application No. PCT/EP2016/059477, which was filed on Apr. 28, 2016, claiming the benefit of priority of to U.S. Provisional Patent Application Serial Number U.S. 62/153,727 filed on Apr. 28, 2015. The contents of each of the aforementioned Patent Applications are incorporated herein by reference in their entirety.

BACKGROUND OF THE INVENTION

Chronic liver diseases, such as liver cirrhosis and hepatocellular carcinoma (HCC) are major challenges for global health. HCC is the second leading and fastest rising cause of cancer death worldwide (International Agency for Research on Cancer; GLOBOCAN 2012: Estimated Cancer Incidence, Mortality and Prevalence Worldwide in 2012— webpage: globocan.iarc.fr). HCC accounts for more than 500,000 new cases per year and nearly as many deaths due to poor disease prognosis. Chronic hepatitis C virus (HCV) infection is the most important risk factor for developing liver cirrhosis and HCC (El-Serag, N Engl J Med., 2011, 365(12): 1118-1127). It is estimated that approximately 3% of the world population is chronically infected with HCV (World Health Organization). Other major risk factors for HCC include infection with hepatitis B virus (HBV), alcoholic liver disease, and non-alcoholic fatty liver disease. A common form of chronic liver disease in Western countries is non-alcoholic fatty liver disease (NAFLD), which encompasses a clinic-pathologic spectrum of diseases ranging from hepatic steatosis to non-alcoholic steatohepatitis (NASH), the more aggressive form of fatty liver disease, which can progress to advanced fibrosis, cirrhosis and its associated complications, including end-stage liver disease and hepatocellular carcinoma. Less common causes include hereditary hemochromatosis, alpha 1-antitrypsin deficiency, autoimmune hepatitis, some porphyrias, Wilson's disease, and aflatoxin exposure. The distribution of these risk factors among patients with HCC is highly variable, depending on geographic region and race or ethnic group. Most of these risk factors lead to the formation and progression of cirrhosis, which is present in 80% to 90% of patients with HCC. The 5-year cumulative risk for the development of HCC in patients with cirrhosis ranges between 5% and 30%, depending on the cause, region or ethnic group, and stage of cirrhosis. In 2011 (see NIH webpage: optn.transplant.hrsa-.gov/latestData/step2.asp), end-stage liver disease and HCC resulted in 6,342 liver transplants associated with costs of more than 1 billion US dollars for the procedure alone.

Although HCC may be avoided by addressing the underlying cause in the early stage of the disease, strategies to prevent liver cirrhosis progression and HCC development in patents with established cirrhosis and advanced fibrosis, in which the risk of liver cirrhosis progression and HCC development persists despite treatment of the underlying cause, are lacking. Indeed, even curing HCV infection does not eliminate the risk of HCC development when advanced fibrosis is already present (van der Meer et al., JAMA, 2012, 308(24): 2584-2593). Currently, curative treatment options for patients with cirrhotic HCC are mainly limited to liver transplantation, an impractical, invasive and resource-intensive solution. Given the extremely frequent tumor recurrence after surgical treatment and the absence of efficient medical treatment strategies, prevention of cirrhosis progression and HCC development in patients with advanced liver fibrosis is considered to be the most effective strategy to substantially impact on patient survival (Hoshida et al., J Hepatol., 2014, 61(1S): S79-S90; Hoshida et al., Curr Cancer Drug Targets, 2012, 12(9):1129-1159).

Molecular biomarkers of liver disease progression in cirrhosis could facilitate the identification of cirrhosis and HCC chemoprotective drugs. Indeed, the Applicants have previously defined and validated a 186-gene stromal liver signature predictive of cirrhosis progression, HCC development, and liver-specific and overall death (as well as a subset thereof comprising 32 genes) in multiple independent cohorts of patients with cirrhosis and HCC caused by HCV and other etiologies including HBV, alcohol and non-alcoholic fatty liver disease (Hoshida et al., New Engl. J. Med., 2008, 359: 1995-2004; Hoshida et al., Gastroenterology, 2013, 144: 1024-103; King et al., Gut, 2015, 64: 1296-1302). This signature was also found to be present in cirrhosis-driven HCC rodent models (Fuchs et al., Hepatology, 2014, 59: 1577-1590), confirming its functional relevance for liver disease and hepatocarcinogenesis in vivo. Pharmacological inhibition of the EGF pathway by a small molecule inhibitor, erlotinib, resulted in chemoprevention of cirrhosis progression and HCC development with subsequent inition of a proof-of-concept clinical trial (ClinicalTrials.gov NCT02273362), although the known toxicities of the drug suggest the need to explore less toxic alternatives. However, the discovery of signature drivers, biomarkers and candidate compounds for the prevention and treatment of cirrhosis progression and HCC development has generally been hampered by the absence of tractable model systems.

In light of the increasing economic burden of patients with cirrhosis and associated HCC, experimental systems modelling HCC-specific gene expression are needed to understand the disease biology and enable disease-specific drug discovery.

SUMMARY OF THE INVENTION

The present invention relates to a cellular model system of cirrhosis progression and HCC development and to its diverse applications. More specifically, using a 186-gene signature and a 32-gene signature predicting >20-year risk of developing HCC, the present Applicants have developed a simple and robust clinical signature-based human cell culture system, in which persistent hepatitis B (HBV) infection, persistent hepatitis C virus (HCV) infection or ethanol exposure induces the prognostic liver signature (PLS) in a reversible manner. Using a computationally enriched small molecule screen in the cell-based system followed by ex vivo validation in human liver tissues, they identified different HCC chemopreventive and anti-cirrhotic agents. The cell-based system, modelling the cell circuits encoded in the clinical HCC risk signature, enables fast-track cancer and cirrhosis chemoprevention/treatment discovery and will improve the dismal prognosis of patients with liver cirrhosis at risk of developing HCC.

Consequently, in one aspect, the present invention provides a method for generating a cellular model for cirrhosis and/or HCC development and progression, said method comprising steps of:

(a) differentiating liver cancer cells to obtain hepatocyte-like cells; and
(b) submitting said hepatocyte-like cells to one hepatocarcinogenic agent to obtain liver cells exhibiting a Prognostic Liver Signature (PLS) high-risk gene signature.

In certain embodiments, the PLS high-risk gene signature is the PLS high-risk 186-gene signature presented in Table 1a, wherein the 73 high-risk genes, or a subset thereof, are overexpressed and the 113 low-risk genes, or a subset thereof, are underexpressed.

In certain embodiments, said liver cancer cells are primary cells isolated from a liver cancer tissue sample or cells from a liver cancer cell line. For example, the liver cancer cell line may be selected from the group consisting of Huh7, Huh106-NTCP, Huh7.5.1, Hep3B.1-7, HepG2, HepG2-NTCP, HepG2AD38, HepG2215, SkHepI, C3A, PLC/PRF/5 and SNU-398 cell lines.

In certain embodiments, differentiation liver cancer cells to obtain hepatocyte-like cells comprises culturing said liver cancer cells in the presence of DMSO. For example, the liver cancer cells may be cultured in the presence of 1% DMSO in the culture medium (vol:vol) for 7 to 10 days.

In certain embodiments, the step of submitting said hepatocyte-like cells to one hepatocarcinogenic agent comprises submitting said hepatocyte-like cells to one of:
persistent HCV infection,
persistent HBV infection, and
ethanol exposure.

In certain embodiments, differentiation of liver cancer cells to obtain hepatocyte-like cells comprises culturing said liver cancer cells in the presence of DMSO. For example, the liver cancer cells may be cultured in the presence of 1% DMSO in the culture medium (vol:vol) for 7 to 10 days.

In certain embodiments, persistent HCV infection is carried out for at least 3 days but less than 60 days and wherein persistent HBV infection is carried out for at least 2 days and less than 15 days.

In certain embodiments, ethanol exposure is carried out in the presence of between 20 mM and 60 mM of ethanol for at least 1 day, but less than 14 days.

In certain embodiments, in step (b), the hepatocyte-like cells are co-cultured with non-parenchymal liver cells.

In certain embodiments, the non-parenchymal liver cells are selected from the group consisting of Kupffer cells, stellate cells, liver resident macrophages, sinusoidal endothelial cells, immune cells, intrahepatic lymphocytes, biliary cells, and any combination thereof.

In another aspect, the present invention relates to a cellular model for cirrhosis/HCC development and progression obtained by a method described herein, wherein said cellular model consists of a substantially homogeneous population of liver cells exhibiting a PLS high-risk signature.

The present invention also relates to a cellular model for cirrhosis/HCC development and progression obtained by a method described herein, wherein said cellular model consists of a heterogeneous population of liver cells consisting of liver cells exhibiting a PLS high-risk signature and non-parenchymal cells.

In certain embodiments, in a cellular model provided herein, the liver cells exhibiting the PLS high-risk gene signature and the non-parenchymal cells are present in a ratio from about 50:50 to about 98:2.

In certain embodiments, in a cellular model provided herein, the PLS high-risk gene signature is the PLS high-risk 186-gene signature presented in Table 1a, wherein the 73 high-risk genes, or a subset thereof, are overexpressed and the 113 low-risk genes, or a subset thereof, are underexpressed.

In another aspect, the present invention provides a screening method for identifying an agent for the treatment or prevention of cirrhosis/HCC, said method comprising steps of:
(1) generating a cellular model for cirrhosis/HCC development and progression using a method according to any one of claims 1 to 11; or providing a cellular model for cirrhosis/HCC development and progression according to any one of claims 12 to 15;
(2) contacting cells of the cellular model with a candidate compound;
(3) determining the effect of the candidate compound on the PLS high-risk gene signature;
(4) identifying the candidate compound as an agent useful for the treatment or prevention of cirrhosis/HCC if the candidate compound transforms the PLS high-risk gene signature of the liver cells to a PLS low-risk signature.

In certain embodiments, the PLS high-risk gene signature is the PLS high-risk 186-gene signature presented in Table 1a, and the candidate compound is identified as an agent useful for the treatment or prevention of cirrhosis/HCC if the candidate compound suppresses the expression of the 73 high-risk genes, or of a subset thereof and/or induces the expression of the 113 low-risk genes, or of a subset thereof.

In other embodiments, the PLS high-risk gene signature is the HCC high-risk 32-gene signature presented in Table 1b, and the candidate compound is identified as an agent useful for the treatment or prevention of cirrhosis/HCC if the candidate compound suppresses the expression of the 19 high-risk genes, or of a subset thereof and/or induces the expression of the 13 low-risk genes, or of a subset thereof.

In certain embodiments, the candidate compound is preselected by in silico drug screening.

In certain embodiments, the signature is inferred from genome wide-analyses (e.g., RNASeq, array). In other embodiments, the signature is inferred from a genome subset (e.g., L1000).

In another aspect, the present invention relates to the use of a cellular model for cirrhosis/HCC development and progression described herein for identifying an agent for the treatment or prevention of cirrhosis/HCC.

The present invention also relates to the use of a cellular model for cirrhosis/HCC development and progression described herein for identifying a cirrhosis/HCC chemopreventive agent.

In yet another aspect, the present invention relates to CI-1040, Captopril, Dilazep, Dorzolamide, Nizatidine, Orteronel, Pimarsertib, Pioglitazone, Rolipram, TG-101348, iBET, C646, or WDR5-0103 for use in the treatment and/or prevention of cirrhosis and/or HCC.

In a related aspect, the present invention relates to a pharmaceutical composition comprising at least one pharmaceutically acceptable carrier or excipient and an effective amount of at least one compound selected from the group consisting of CI-1040, Captopril, Dilazep, Dorzolamide, Nizatidine, Orteronel, Pimarsertib, Pioglitazone, Rolipram, TG-101348, iBET, C646, and WDR5-0103 for use in the treatment or prevention of cirrhosis and/or HCC.

In another related aspect, the present invention relates to a method for treating or preventing cirrhosis/HCC in a subject comprising a step of:
administering to said subject an effective amount of at least one compound selected from the group consisting of CI-1040, Captopril, Dilazep, Dorzolamide, Nizatidine, Orteronel, Pimasertib, Pioglitazone, Rolipram, TG-101348, iBET, C646, and WDR5-0103, or a pharmaceutical composition thereof.

In another aspect, the present invention relates to the use of a cellular model for cirrhosis/HCC development and progression provided herein for identifying a biomarker of cirrhosis/HCC progression or development.

The Applicants have also shown that non-hepatic cancer cell lines, including colon (Caco-2/TC7) and cervical (HeLa) cells can be used as a model to express a Prognostic Liver Signature (PLS) following ethanol exposure.

Accordingly, the present invention provides a method for generating a cellular model, said method comprising steps of:
(a) providing non-hepatic cancer cells;
(b) submitting said non-hepatic cancer cells to ethanol to obtain non-hepatic cells exhibiting a PLS high-risk gene signature.

In certain embodiments, the PLS high-risk gene signature is the PLS high-risk 186-gene signature presented in Table 1a, wherein the 73 high-risk genes, or a subset thereof (for example the 19 PLS high-risk genes of Table 1b), are overexpressed and the 113 low-risk genes, or a subset thereof (for example the 13 PLS low-risk genes of Table 1b), are underexpressed.

In certain embodiments, the non-hepatic cancer cells are cells from any cancer cell line. For example, the cancer cell line may be the CaCo cell line or the Hela cell line.

The present invention also relates to the use of a cellular model obtained as described above from non-hepatic cancer cells for identifying an agent for the treatment or prevention of a non-hepatic cancer.

The present invention also relates to a screening method for identifying an agent for the treatment or prevention of a non-hepatic cancer, said method comprising steps of:
(1) generating a cellular model using a method described above (from non-hepatic cancer cells);
(2) contacting cells of the cellular model with a candidate compound;
(3) determining the effect of the candidate compound on the PLS high-risk gene signature;
(4) identifying the candidate compound as an agent useful for the treatment or prevention of a non-hepatic cancer if the candidate compound transforms the PLS high-risk gene signature of the liver cells to a PLS low-risk signature.

These and other objects, advantages and features of the present invention will become apparent to those of ordinary skill in the art having read the following detailed description of the preferred embodiments.

DEFINITIONS

Figure 1:
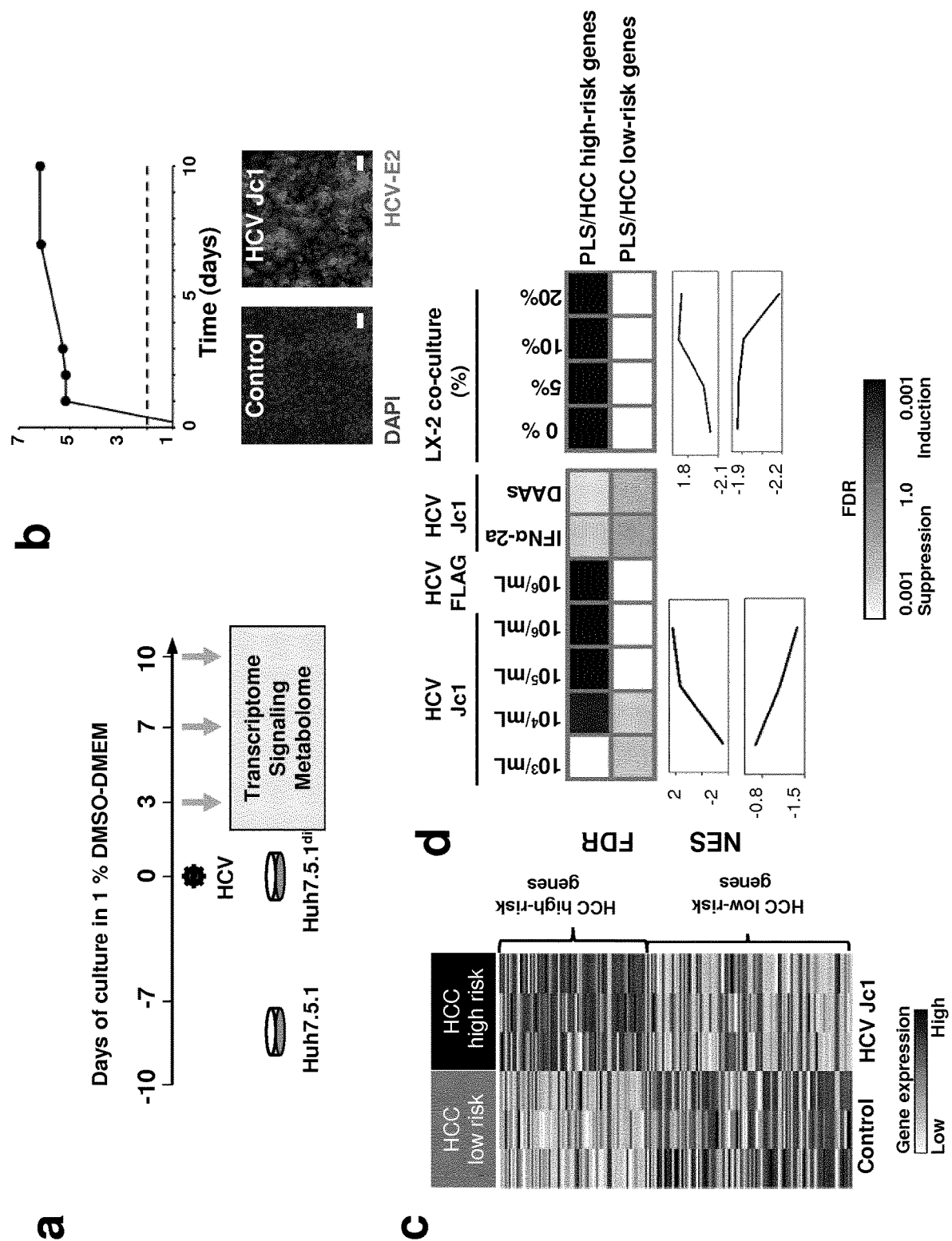
FIG. 1. Modeling the transcriptional profiling of cirrhotic patients progressing to HCC or cirrhosis in a simple and robust liver cell-based system. a. Approach. Huh7.5.1 cells were differentiated into Huh7.5.1$^{dif}$ cells, persistently infected using HCV Jc1 and subjected to molecular analyses at different time points post-infection. b. Top panel: analysis of HCV infection by qRT-PCR of HCV RNA (mean±s.d.; n=3). Given the very low standard deviations, the error bars are not visible on the graph. The dashed line indicates the limit of detection (top panel). Bottom panel: immunodetection of HCV E2 protein at day 10 post-infection. Nuclei were counterstained with DAPI. Scale bar, 50 µm. The results shown are representative of one out of two experiments. c. 186-gene prognostic liver signature (PLS) assay in Huh7.5.1$^{dif}$ cells. Heatmap shows high (black) and low (white) gene expression across samples. HCV Jc1-infected (HCV Jc1) and non-infected (Control) cells were predicted as PLS high-risk or low-risk as described in the Materials and Methods section. The results shown are representative of one out of three independent experiments performed in triplicate. d. Heatmap (top) and plots (bottom) showing the significance of high-/low-risk genes induction/suppression under persistent infection of cells using increasing titers of HCV Jc1; highly purified HCV particles (HCV Jc1E2$^{FLAG}$); following antiviral treatment using IFNα-2a or DAAs; or following co-culture with increasing percentages of hepatic stellate LX-2 cells. In scale bar, dense black indicates significant induction, white indicates significant suppression. For each condition, the results shown are representative of one experiment performed in triplicate. FDR: false discovery rate; NES: normalized enrichment score.

Throughout the specification, several terms are employed that are defined in the following paragraphs.

The terms "hepatocellular carcinoma" and "HCC" are used herein interchangeably. They refer to the most common type of liver cancer, also called malignant hepatoma. HCC can be secondary to infection with hepatitis C virus (HCV), or secondary to hepatitis B virus (HBV) infection, alcoholic liver disease, non-alcoholic fatty liver disease, hereditary hemochromatosis, alpha 1-antitrypsin deficiency, auto-immune hepatitis, some porphyrias, Wilson's disease, aflatoxin exposure, type 2 diabetes, obesity, etc. . . . .

As used herein, the term "hepatocarcinogenic" has its art understood meaning and characterizes an agent or a factor that produces or causes, or tends to produce or cause, cancer of the liver or a liver disease that can progress to cancer of the liver. As indicated above, hepatocarinogenic agents or factors include a variety of ethiological agents such as viral hepatitis (primarily hepatitis B and C), alcohol abuse, hemochromatosis, certain autoimmune diseases of the liver, non-alcoholic fatty liver diseases, non-alcoholic steatohepatitis, chemical carcinogens such as aflatoxin, and other diseases that result in chronic inflammation of the liver and scarring. In most embodiments of the present invention, the term "hepatocarcinogenic agent" more specifically refers to an agent that can be used to cause a liver cell to become cancerous in vitro.

As used herein, the terms "cells" refers to cells in various forms, including but not limited to cells retained in tissues, cell clusters, and individually isolated cells. The term "isolated", when used herein to characterize cells, means cells which, by virtue of their origin or manipulation, are separated from at least some of the components with which they are naturally associated or with which they are associated when initially obtained or prepared. In the context of the invention, liver cancer cells are used to prepare the cellular model system of HCC development and progression. The term "liver cancer cells" refers to cells that have been isolated from a liver tumor or liver cancer sample (e.g., a biopsy sample) or to cells from a liver tumor-derived cell line or from a liver cancer-derived cell line.

As used herein, the term "non parenchymal cell" refers to any cell that is not a parenchymal cell. In the liver, non-parenchymal cells produce key paracrine factors that influence growth, metabolism, and transport functions in hepatocytes. Non-parenchymal liver cells include Kupffer cells, stellate cells, liver resident macrophages, sinusoidal endothelial cells, immune cells (T, B, NK cells and the like), intrahepatic lymphocytes, and biliary cells as well as cell lines modelling non-parenchymal liver cells.

As used herein, the term "gene" refers to a polynucleotide that encodes a discrete macromolecular product, be it a RNA or a protein, and may include regulatory sequences preceding (5' non-coding sequences) and following (3' non-coding sequences) the coding sequence. As more than one polynucleotide may encode a discrete product, the term "gene" also includes alleles and polymorphisms of a gene that encode the same product, or a functionally associated (including gain, loss or modulation of function) analog thereof.

The term "gene expression" refers to the process by which RNA and proteins are made from the instructions encoded in genes. Gene expression includes transcription and/or translation of nucleic acid material. The terms "gene expression pattern" and "gene expression profile" are used herein interchangeably. They refer to the expression (i.e., to the level or amount or copy number) of an individual gene or of a set of genes. A gene expression pattern may include information regarding the presence of target transcripts in a sample, and the relative or absolute abundance levels of target transcripts.

As used herein, the term "subject" refers to a human or another mammal (e.g., primate, dog, cat, goat, horse, pig, mouse, rat, rabbit, and the like), that can develop HCC, but may or may not be suffering from the disease. Non-human subjects may be transgenic or otherwise modified animals.

In preferred embodiments of the present invention, the subject is a human being. In such embodiments, the subject is often referred to as an "individual" or a "patient". The term "individual" does not denote a particular age, and thus encompasses newborns, children, teenagers, and adults. The term "patient" more specifically refers to an individual suffering from a disease (e.g., a liver disease).

The term "treatment" is used herein to characterize a method or process that is aimed at (1) delaying or preventing the onset of a disease or condition (e.g., hepatocellular carcinoma); (2) slowing down or stopping the progression, aggravation, or deterioration of the symptoms of the disease or condition (e.g., liver disease or cirrhosis); (3) bringing about amelioration of the symptoms of the disease or condition; or (4) curing the disease or condition. A treatment may be administered after initiation of the disease or condition, for a therapeutic action. Alternatively, a treatment may be administered prior to the onset of the disease or condition, for a prophylactic or preventive action. In this case, the term "prevention" is used.

As used herein, the term "HCC/cirrhosis chemopreventive agent", refers to any agent that can prevent or inhibit cirrhosis and/or HCC from developing or progressing or that can reduce the likelihood of cirrhosis and/or HCC from developing or from progressing.

The term "candidate compound" refers to any naturally occurring or non-naturally occurring molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues to be tested for an activity of interest. In the screening methods of the invention, candidate compounds are evaluated for their ability to modulate the expression of genes of a Prognostic Liver Signature (PLS).

The term "small molecule", as used herein, refers to any natural or synthetic organic or inorganic compound or factor with a low molecular weight. Preferred small molecules have molecular weights of more than 50 Daltons and less than 2,500 Daltons. More preferably, small molecules have molecular weights of less than 600-700 Daltons. Even more preferably, small molecules have molecular weights of less than 350 Daltons.

A "pharmaceutical composition" is defined herein as comprising an effective amount of an agent that has been identified by a method of screening of the invention to be useful in the treatment or prevention of cirrhosis/HCC, and at least one pharmaceutically acceptable carrier or excipient.

As used herein, the term "effective amount" refers to any amount of an agent or pharmaceutical composition thereof that is sufficient to fulfil its intended purpose(s), e.g., a desired biological or medicinal response in a cell, tissue, system or subject. For example, in certain embodiments of the present invention, the purpose(s) may be: to modulate the expression of genes of a Prognostic Liver Signature (PLS) in the cellular model system of the invention (e.g., to cause the suppression of PLS high-risk genes and/or to cause the induction or overexpression of PLS low-risk genes); and/or to prevent, inhibit or reduce the likelihood of cirrhosis and/or HCC from developing or from progressing.

The term "pharmaceutically acceptable carrier or excipient" refers to a carrier medium which does not interfere with the effectiveness of the biological activity of the active ingredient(s) and which is not significantly toxic to the host at the concentration at which it is administered. The term includes solvents, dispersion, media, coatings, antibacterial and antifungal agents, isotonic agents, and adsorption delaying agents, and the like. The use of such media and agents for pharmaceutically active substances is well known in the art (see for example "*Remington's Pharmaceutical Sciences*", E. W. Martin, 18$^{th}$ Ed., 1990, Mack Publishing Co.: Easton, Pa., which is incorporated herein by reference in its entirety).

The terms "approximately" and "about", as used in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As indicated above, the present invention provides a simple and robust signature-based human cell culture system that models the clinical cell circuits of liver disease progression in a reversible manner. This cell culture model finds application in screening methods for identifying drugs for the treatment or prevention of cirrhosis and/or HCC, and as a research tool to identify and study candidate drivers of the cirrhosis/HCC risk signature.

I—Preparation of a Prognostic Liver Signature (PLS)-Based Cell Culture System

The present Applicants have developed a method for generating a cellular model for cirrhosis and/or HCC development and progression. The method generally comprises a step of differentiating liver cancer cells to obtain hepatocyte-like cells; and a step of submitting the hepatocyte-like cells to a hepatocarcinogenic agent to obtain liver cells exhibiting a PLS high-risk gene signature. In certain embodiments, the hepatocyte-like cells are submitted to a hepatocarcinogenic agent while being co-cultured with non-parenchymal liver cells.

PLS High-Risk Signature

A method according to the present invention yields liver cells that exhibit a PLS high-risk gene signature.

The term "Prognostic Liver Signature (PLS)", as used herein, refers to molecular biomarkers, gene expression or any other means for identification or prediction of cirrhosis progression and/or HCC development, and more specifically refers to the 186-gene stromal liver signature predictive of HCC development, cirrhosis progression and liver-specific and overall death previously developped by the present Applicants and described in Hoshida et al., New Engl. J. Med., 2008, 359: 1995-2004; Hoshida et al., Gastroenterology, 2013, 144: 1024-103; King et al., Gut, 2015, 64: 1296-1302; Fuchs et al., Hepatology, 2014, 59: 1577-1590, or a subset thereof. Table 1a, which is presented in the Examples section below, provides the identity of the 186 genes of the signature, which consists of 73 PLS high-risk genes and 113 PLS low-risk genes. As used herein, the term "PLS high-risk genes" refers to genes of the signature whose overexpression correlates with high risk of future cirrhosis progression, HCC development, and poorer liver-specific and overall survival, and the term "PLS low-risk genes" refers to genes whose overexpression correlates with absence or low risk of future HCC development or progression and good survival.

The term "liver cells exhibiting a PLS high-risk gene signature", as used herein to characterize liver cells of a cellular model for cirrhosis/HCC development and progression according to the invention, refers to cells in which the 73 PLS high-risk genes of Table 1a, or a subset thereof, are overexpressed, and in which the 113 PLS low-risk genes of Table 1a, or a subset thereof, are underexpressed.

In contrast, the term "liver cells exhibiting a PLS low-risk gene signature", as used herein to characterize liver cells (for example hepatocyte-like cells obtained by differentiation according to the invention), refers to cells in which the 73 PLS high-risk genes of Table 1a, or a subset thereof, are underexpressed and in which the 113 PLS low-risk genes of Table 1a, or a subset thereof, are overexpressed.

As used herein, the term "a subset of the PLS 186-gene signature" refers to any subset or subgroup of the 186 genes that can be used to predict cirrhosis/HCC development in a patient with liver disease. In certain embodiments, a subset of the PLS 186-gene signature is a 32-gene signature which was derived from the 186-gene PLS-risk signature and which has been shown to exhibit a high significance for prediction of liver disease progression, cirrhosis progression, HCC development, and death in all major HCC etiologies (HCV, HBV, alcohol and NASH) (King et al., Gut, 2014, 64(8): 1296-1302). Table 1b, presented in the Examples section below, provides the identity of the 32 genes of the signature, which consists of 19 PLS high-risk genes and 13 PLS low-risk genes.

Liver Cancer Cells

One skilled in the art will understand that the present invention may be applied to the generation of a non-human mammalian cellular model for cirrhosis/HCC development and progression. However, preferably the cellular model is a cellular model for cirrhosis/HCC development and progression in humans. Consequently, the present document mainly relates to a human cellular model.

The starting material in a method described herein is liver cancer cells. Liver cancer cells that may be used for generating a cellular model for cirrhosis/HCC development and progression include primary cells (i.e., liver cells taken directly from living tissue—e.g., hepatocytes isolated from biopsy material), secondary cells (i.e., liver cells obtained from primary cells by sub-culture), and immortalized cells (e.g., established liver cell lines). The liver cells may be obtained and prepared by techniques well known in the art or purchased from immunological and microbiological commercial resources (for example from the American Type Culture Collection, USA).

In preferred embodiments, the liver cancer cells to be used in a method for generating a cellular model for cirrhosis/HCC development and progression are cells from a human liver cancer cell line. Examples of human liver cancer cell lines include, but are not limited to, the Huh7 cell line and its derivatives, e.g., Huh7.5, Huh7.5.1, and Huh106; the Hep3b cell line and its derivatives, e.g., Hep3B.1-7; the HepG2 cell line and its derivatives, e.g., HepG2/2.2.1, HepG2-NTCP, HepG2AD38, HepG2215, and Hep G2T14; the liver adenocarcinoma SkHepI; the C3A cell line; the Alexander hepatoma cell line PLC/PRF/5; the SNU cell lines (e.g., the SNU-398 cell line) and the like. In certain preferred embodiments, the liver cancer cell line used to generate a human cellular model for cirrhosis/HCC development and progression according to the invention is Huh7 or Huh7.5.1 (as described in the Examples below).

Generally, prior to being used in a method according to the present invention, the liver cells are grown according to standard cell culture techniques. For example, cells are often grown in an appropriate culture medium in a suitable vessel in a sterile environment at 37° C. in an incubator containing a humidified 95% air—5% $CO_2$ atmosphere. Vessels may contain stirred or stationary cultures. Cell culture techniques are well known in the art and established protocols are available for the culture of diverse cell types (see for example, R. I. Freshney, "Culture of Animal Cells: A Manual of Basic Technique", $2^{nd}$ Edition, 1987, Alan R. Liss, Inc.). As used herein, the term "appropriate culture medium" refers to a culture medium that contains nutrients necessary to support the growth and/or survival of the culture cells. An appropriate culture medium may or may not contain growth factors. An appropriate culture medium according to the invention may consist in a minimal medium in which cells can be alive and grow, such as for example Dulbecco's Modified Eagle Medium (DMEM) supplemented or not with decomplemented fetal calf serum (FCS). Alternatively, an appropriate medium may be a primary hepatocyte maintenance medium (PMM).

If desired, cell viability can be determined prior to using the liver cancer cells for generating a cellular model for cirrhosis/HCC development and progression. Standard techniques, such as histology, quantitative assessment with radioisotopes, visual observation using a light or scanning electron microscope or a fluorescent microscope, may be used to determine cell viability. Alternatively, cell viability may be assessed by Fluorescence-Activated Cell Sorting (FACS).

In certain embodiments, prior to being used in a method of the invention, the liver cancer cells are genetically engineered to become susceptible, or more susceptible, to a particular hepatocarcinogenic agent. For example, cells from a liver cell line may be engineered to become susceptible, or more susceptible, to HBV infection. The term "HBV susceptible cell", as used herein, refers to a cell that can be infected with HBV. One way to confer susceptibility to HBV and HDV is to genetically engineer cells to over-express NTCP (sodium tautocholate cotransporting polypeptide), a functional cell receptor for HBV and HDV (Yan et al., eLife, 2012, 1:e00049) (see Examples section below).

It is worth noting that the present Applicants have also shown that non-hepatic cell lines, including colon (Caco-2/TC7) and cervical (HeLa) cells can be used as a model to express a Prognostic Liver Signature (PLS) (see Examples). In such embodiments, the non-hepatic cell lines do not need to undergo differentiation before being submitted to ethanol.

Differentiation of Liver Cancer Cells

In a method according to the invention, the step of differentiation may be performed by culturing liver cancer cells in the presence of DMSO. The Applicants have found that short-term differentiation of 7-10 days already resulted in differentiation of liver cells into hepatocyte-like cells.

The step of differentiation is generally carried out for a time and under conditions allowing the liver cancer cells to differentiate (i.e., allowing induction of a liver tissue-specific gene signature and suppression of cancerous (e.g., HCC) tissue-specific gene signature in the cells or allowing the cells to undergo a shift from a malignant to a non-malignant hepatocyte profile).

The cells are generally cultured in the presence of from about 0.1% to about 3% DMSO (vol:vol in the cell culture medium), in particular about 0.1%, about 0.2%, about 0.3%, about 0.4%, about 0.5%, about 0.75%, about 0.8%, about 0.9%, about 1%, about 1.2%, about 1.3%, about 1.4%, about 1.5%, about 1.6%, about 1.7%, about 1.8%, about 1.9%, about 2%, about 2.25%, about 2.5%, about 2.75%, or about 3% DMSO. The step of differentiation is carried out for about 3 days to no more than 60 days, for example for about 4 days, about 5 days, about 6 days, about 7 days, about 8 days, about 9 days, about 10 days, about 11 days, about 12 days, about 13 days, about 14 days, or 15 days, or more than 15 days, for example about 20 days, about 30 days, about 40 days, or about 60 days. For example, when the starting liver cancer cells are cells from the Huh7.5.1 cell line, the step of differentiation may be carried out in the presence of 1% DMSO for up to 10 days. Depending on the nature of the starting liver cells, one skilled in the art knows how to select and optimize the differentiation conditions to obtain hepatocyte-like cells.

As used herein, the term "hepatocyte-like cell" refers to a cell (a single cell or a population of cells), in particular a cell that is obtained by liver cancer cells differentiation as described herein, and that is positive for (i.e., that exhibits) one or more hepatocyte characters. Hepatocyte characters include, but are not limited to:

(1) Expression of one or more hepatocyte markers (e.g., glucose-6-phosphatase, albumin (ALB), alpha-1-antitrypsin (ATT, also known as SERPINA1), cytokeratin 8 (CK8), cytokeratin 18 (CK18), cytokeratin 8/18 (CK8/18), asialoglycoprotein receptor 1 (ASGR1), alcohol dehydrogenase 1, arginase Type 1, cytochrome p450 3A4 (CYP3A4), liver-specific organic anion transporter (LST-1), forkhead box protein A2 (FoxA2), alphafetoprotein (AFP), tryptophan 2,3-dioxygenase (TD02), and combinations thereof);
(2) Activity of liver enzymes such as glucose-6-phosphatase, CYP3A4 and/or CYP 1A1;
(3) Production and/or secretion of liver products (e.g., as measured in bodily fluids such as blood serum, plasma, etc (e.g., bile, urea, and/or albumin);
(4) Exhibition of a hepatocyte metabolic property (e.g., ability to detoxify xenobiotics, endocytosis of LDL, synthesis of glycogen, cytochrome P450 1A2 detoxification activity, and the like);
(5) Exhibition of hepatocyte morphological features;
(6) Ability to engraft into the liver of an immunodeficient individual (e.g., a mouse, a human, etc); and
(7) Lack of expression of (negative for) one or more non-hepatocyte markers (e.g., adipocyte markers, e.g., CD37, CD29, etc. . . . ; ASC markers, e.g., CD105, and the like).

Submitting Hepatocyte-Like Cells to a Hepatocarcinogenic Agent

In the second step of the method for generating a cellular model for cirrhosis/HCC development and progression, hepatocyte-like cells, which were obtained by differentiation of liver cancer cells, are submitted to a hepatocarcinogenic agent. As used herein, the term "submitting cells to a hepatocarcinogenic agent" refers to a process in which cells are exposed to (e.g., contacted with and/or incubated with and/or grown in the presence of) a hepatocarcinogenic agent while being cultured. The exposure or contact is performed under conditions and for a time sufficient for the hepatocarcinogenic agent to induce the desired effect (i.e., to induce a stable PLS high-risk gene signature in the cells). The hepatocarcinogenic agent may be any suitable hepatocarcinogenic agent, and its mechanism of action is not a limiting factor.

In certain embodiments of the invention, submitting hepatocyte-like cells to a hepatocarcinogenic agent may be: submitting said hepatocyte-like cells to persistent HCV infection. Methods for infecting cells (including liver cells) with HCV are known in the art (Wakita et al., Nature Medicine, 2005, 11: 791-796). The Examples section below provides a description of a method for infecting differentiated cells from the Huh7.5.1 cell line with HCVcc Jc1 at a multiplicity of infection of between $10^4$ and $10^9$ for at least 5 to 10 days. The Applicants have found that when cells are differentiated with DMSO for a short period of time (about 7-10 days) and then infected with HCV for a short period of time (about 10 days), the PLS risk signature is efficiently induced. HCV infection of the cells may be assessed using any suitable method, such as for example by qRT-PCR of intracellular HCV RNA in cell lysates and/or by immunostaining, for example using a HCV E2-specific antibody.

In other embodiments of the invention, submitting hepatocyte-like cells to a hepatocarcinogenic agent may be: submitting said hepatocyte-like cells to persistent HBV infection. As already mentioned above, to prepare a cellular model for cirrhosis/HCC development and progression by HBV infection, the starting cells must be HBV susceptible cells (i.e., must be cells that are intrinsically susceptible to HBV infection or cells that have been genetically engineered to overexpress NTCP). Methods for infecting cells (including liver cells) with HBV are known in the art (Verrier et al., Hepatology, 2015, 63: 35-48; Yan et al., eLife, 2012 Nov. 13; 1:e00049). The Examples section below provides a method for infecting NTCP-overexpressing HepG2 cells with HBV purified from the serum of a HBV-infected patient at a multiplicity of infection of between $10^2$ and $10^8$ for 2-10 days. HBV infection of the cells may be assessed using any suitable method, such as for example by qRT-PCR quantification of HBV pregenomic RNA, Southern blog or RCR of HBV-DNA in cell lysates and/or by immunodetection of HBsAg or HBcAg (hepatitis B surface antigen, hepatitis B core antigen) using a HBsAg-specific monoclonal antibody).

In yet other embodiments of the invention, submitting hepatocyte-like cells to a hepatocarcinogenic agent may be: submitting said hepatocyte-like cells to ethanol exposure. Ethanol may be used at any suitable concentration and the exposure may be performed for any suitable time. For example, the cells may be exposed to about 20 mM, about 25 mM, about 30 mM, about 35 mM, about 40 mM, about 45 mM or about 60 mM or more of ethanol, for at least 1 day and less than 14 days. Preferably, fresh medium containing ethanol is replenished every day. The Examples section below provides a method for exposing cells to ethanol.

During the step where the hepatocyte-like cells are submitted to a hepatocarcinogenic agent, DMSO may be present in the cell culture medium (e.g., at a concentration of between about 0.1% to about 3% DMSO vol:vol in the cell culture medium).

Co-Culture with Non-Parenchymal Liver Cells

In certain embodiments, step (b) of a method for generating a cellular model for cirrhosis/HCC development and progression according to the invention is performed while the hepatocyte-like cells are co-cultured with non-parenchymal liver cells. It is known in the art that co-culture of hepatocytes with non-parenchymal liver cells better represent both normal in vivo liver physiology and disease states. The present Applicants have found that, in addition to further improve the in vitro liver cell model, the presence of non-parenchymal liver cells enhances the induction of the PLS high-risk gene signature in a cell- and dose-dependent manner. While hepatocytes alone are sufficient for generating the PLS high-risk gene signature by exposure to a hepatocarcinogenic agent, this can be amplified through cross-talk with non-parenchymal cells.

By "enhance PLS high-risk gene signature induction" or "amplify PLS high-risk gene signature induction" is meant herein that co-culture of hepatocyte-like cells with non-parenchymal cells induces an increase in the over-expression of at least one PLS high-risk gene of the PLS and/or an increase in the number of over-expressed PLS high-risk genes of the PLS. The term "an increase in the over-expression of at least one PLS high-risk gene of the PLS", as used herein, refers to an amount of said PLS high-risk gene over-expressed by liver cells co-cultured with non-parenchymal cells that is higher than the amount of said PLS high-risk gene over-expressed by liver cells cultured in the absence of non-parenchymal liver cells, all other things being equal. In certain embodiments, the amount of said over-expressed PLS high-risk gene in the co-culture is at least 1.25 times higher than the amount of said over-expressed PLS high-risk gene in the mono-culture, all other things being equal. For example, the increase in the amount may be by a factor of about 1.5, about 1.75, about 2, about 2.5, about 3, about 4 about, 5, about 6, about 7, about 8, about 9, about 10 or more than 10. The term "an increase in the number of over-expressed PLS high-risk genes of the PLS", as used herein, refers to a number of PLS high-risk genes over-expressed by liver cells co-cultured with non-parenchymal cells that is higher than the number of PLS high-risk genes over-expressed by liver cells cultured in the absence of non-parenchymal cells, all other things being equal. In certain embodiments, the number of PLS high-risk genes that is over-expressed in the co-culture is at least 1.25 times higher than the number of high-risk genes that is over-expressed in the mono-culture, all other things being equal. For example, the increase in the number may be by a factor of about 1.5, about 1.75, about 2, about 2.5, about 3, about 4 about, 5, about 6, about 7, about 8, about 9, about 10 or more than 10.

By the terms "enhance PLS high-risk gene signature induction" or "amplify PLS high-risk gene signature induction" is also meant herein that co-culture of hepatocyte-like cells with non-parenchymal cells induces an increase in the under-expression of at least one PLS low-risk gene of the PLS and/or an increase in the number of under-expressed PLS low-risk genes of the PLS. The term "an increase in the under-expression of at least one PLS low-risk gene of the PLS" as used herein, refers to an amount of said PLS low-risk gene under-expressed by liver cells co-cultured with non-parenchymal cells that is higher than the amount of said PLS low-risk gene under-expressed by liver cells cultured in the absence of non-parenchymal liver cells, all other things being equal. In certain embodiments, the amount of said under-expressed PLS low-risk gene in the co-culture is at least 1.25 times higher than the amount of said under-expressed PLS low-risk gene in the mono-culture, all other things being equal. For example, the increase in the amount may be by a factor of about 1.5, about 1.75, about 2, about 2.5, about 3, about 4 about, 5, about 6, about 7, about 8, about 9, about 10 or more than 10. The term "an increase in the number of under-expressed PLS low-risk genes of the PLS", as used herein, refers to a number of PLS low-risk genes under-expressed by liver cells co-cultured with non-parenchymal cells that is higher than the number of PLS low-risk genes under-expressed by liver cells cultured in the absence of non-parenchymal cells, all other things being equal. In certain embodiments, the number of PLS low-risk genes that is under-expressed in the co-culture is at least 1.25 times higher than the number of low-risk genes that is under-expressed in the mono-culture, all other things being equal. For example, the increase in the number may be by a factor of about 1.5, about 1.75, about 2, about 2.5, about 3, about 4 about, 5, about 6, about 7, about 8, about 9, about 10 or more than 10.

As intended herein, the term "co-culturing" refers to a process in which at least two different types of cells are cultured together in an appropriate culture medium. In the context of the present invention, hepatocyte-like cells (obtained by differentiation of liver cancer cells) are co-cultured with non-parenchymal liver cells.

The hepatocyte-like cells and non-parenchymal liver cells may be co-cultured in any suitable ratio, i.e., in any ratio that enhances or amplifies the PLS high-risk gene signature induction. For example, in certain embodiments, hepatocyte-like cells and non-parenchymal liver cells may be co-cultured in a ratio from about 1:99 to about 99:1, for example, about 5:95, about 10:90, about 20:80, about 25:75; about 30:70; about 40:60; about 50:50; about 60:40; about 70:30; about 75:25, about 80:20, about 90:10 or about 95:5.

Non-parenchymal liver cells that can be used in the context of the present invention include, but are not limited to Kupffer cells, stellate cells, liver resident macrophages, sinusoidal endothelial cells, immune cells (T, B, NK cells and the like), intrahepatic lymphocytes, and biliary cells as well as cell lines modelling non-parenchymal liver cells. In certain embodiments, the non-parenchymal cells co-cultured with the hepatocyte-like cells are of a single cell type (e.g., hepatic stellate cells). In other embodiments, non-parenchymal cells co-cultured with the hepatocyte-like cells are a mixture of different types of non-parenchymal cells (e.g., hepatic stellate cells and sinusoidal endothelial cells or hepatic stellate cells and Kupffer cells).

Generally, hepatocyte-like cells and non-parenchymal liver cells are co-cultured under conditions where they are in physical contact. As used herein, the term "physical contact" has its general meaning. For example, cells are in physical contact with each other when they are in a conformation or arrangement that allows for intercellular exchange of materials and/or information to take place.

The conditions of the co-culture (of hepatocyte-like cells and non-parenchymal cells) may be identical to the conditions of the monoculture (of hepatocyte-like cells alone), as described above, or may be modified as long as these conditions do not interfere with the action of the hepatocarcinogenic agent.

In certain embodiments, at the end of the co-culture, the liver cells that exhibit the PLS high-risk gene signature are separated from the non-parenchymal cells with which they were co-cultured. In other embodiments, the co-culture (comprising the liver cells that exhibit the PLS high-risk gene signature and the non-parenchymal cells) is used without any further modification (in particular without any isolation or separation step).

Liver Cells Exhibiting a PLS High-Risk Signature

In certain embodiments, a method for generating a cellular model for cirrhosis/HCC development and progression according to the present invention further comprises a step of characterizing the cells obtained, and more specifically verifying that the cells do indeed exhibit a PLS high-risk gene signature, i.e., verifying that the 73 PLS high-risk genes of Table 1a, or a subset thereof (for example the 19 PLS high-risk genes of Table 1b), are induced or overexpressed, and/or that the 113 PLS low-risk genes of Table 1a, or a subset thereof (for example the 13 PLS high-risk genes of Table 1b), are suppressed or under-expressed.

This verification can be performed using any of a variety of suitable methods known in the art for gene expression analysis. In certain embodiments, this verification is performed by Gene Set Enrichment Analysis (GSEA) (Subramanian et al., PNAS USA, 2005, 102: 15545-15555), a computational method that determines whether a defined set of genes shows statistically significant, concordant differences between two biological states (e.g., before being differentiated, after being differentiated and after being submitted to a hepatocarcinogenic agent).

Storage

If desired, the liver cells, either following differentiation with DMSO or following exposure to a hepatocarcinogenic agent can be cryopreserved for future use. In such case, the cells are preferably cryopreserved under such conditions that most of the cells are viable upon recovery (i.e., thawing). Preferably, more than about 80%, more than about 85% or more than about 90% (e.g., 95%, 97%, 98%, or 99% or more) of the cryopreserved cells are viable after recovery. Preferably, the cryopreservation conditions are such that viable cells have identical morphologic and functional characteristics as the cells prior to cryopreservation.

Methods for the cryopreservation of different types of cells are known in the art. Any suitable method of cryopreservation may be used in the practice of the present invention. Typically, the cryopreservation medium contains dimethyl sulfoxide (DMSO). The cryopreservation medium may further comprise cryopreservation agents such as, methylcellulose. Once frozen, the cells may be stored indefinitely under liquid nitrogen until needed, as long as care is taken to prevent the possibility of accidental thawing or warming of the frozen cells at any time during their storage period.

When the cells are to be used in a method of the present invention (e.g., a screening method), they can be thawed under controlled conditions, for example by transferring the vial(s) containing frozen cells to a water bath set at 37° C. The thawed contents of the vial(s) may then be rapidly transferred under sterile conditions to a culture vessel containing an appropriate medium. The thawed cells can then be tested for viability, growth properties, etc.

II—Prognostic Liver Signature (PLS)-Based Cell Culture Systems

In another aspect, the present invention relates to a robust cellular model for cirrhosis/HCC development and progression, in particular a cellular model for HCC development and progression in humans, obtained using a method described herein. A cell model according to the invention comprises liver cells exhibiting a PLS high-risk gene signature.

In certain embodiments, the cellular model consists of a substantially homogenous population of liver cells exhibiting a PLS high-risk gene signature. The term "substantially homogeneous population", as used herein in relation to a population of liver cells of a cellular model of the invention, refers to a population of a single type of cells, and more specifically to a population of liver cells obtained using a method of the invention wherein the majority (e.g., at least about 80%, preferably at least about 90%, more preferably at least about 95%, and even more preferably at least about 98%) of the total number of liver cells exhibit the PLS high-risk gene signature.

In other embodiments, the cellular model consists of a heterologous population of liver cells. The term "heterologous population", as used herein in relation to a population of liver cells of a cellular model of the invention, refers to a mixture of two different types of cells, and more specifically to a mixture of liver cells exhibiting the PLS high-risk gene signature and of non-parenchymal cells. The liver cells exhibiting the PLS high-risk gene signature and the non-parenchymal cells may be present in a ratio from about 1:99 to about 99:1, for example, about 5:95, about 10:90, about 20:80, about 25:75; about 30:70; about 40:60; about 50:50; about 60:40; about 70:30; about 75:25, about 80:20, about 90:10 or about 95:5.

III—Applications of the Prognostic Liver Signature (PLS)-Based Cell Culture System The cell models described herein can find applications in screening methods for identifying agents for the treatment or prevention of cirrhosis/HCC, and as a research tool for identifying and studying candidate drivers of the PLS.

Screening and Identification of Cirrhosis/HCC Therapeutic or Preventive Agents

Thus, the present invention provides a method for identifying agents that are useful in the treatment or prevention of cirrhosis/HCC, in particular for identifying agents to prevent and/or cirrhosis and/or HCC. A method for identifying an agent useful for the treatment or preventing of cirrhosis/HCC generally comprises steps of: generating a cellular model for cirrhosis/HCC development and progression using a method described herein or providing a cellular model for cirrhosis/HCC development and progression described herein; contacting the liver cells from the cellular model with a candidate compound; determining the effect of the candidate compound on the PLS high-risk gene signature; and identifying the candidate compound as an agent useful for the treatment or prevention of cirrhosis/HCC if the candidate compound suppresses the expression of the 73 PLS high-risk genes of Table 1a, or a subset thereof, and/or induces the expression of the 113 PLS low-risk genes of Table 1a, or a subset thereof. In other words, in a method of the present invention, a candidate compound is identified as an agent useful for the treatment or prevention of cirrhosis/HCC if the candidate compound exhibits the ability to transform the PLS high-risk signature of the liver cells into a PLS low-risk signature.

Contacting Liver Cells with a Candidate Compound

In certain embodiments, the screening methods are performed using cells contained in a plurality of wells of a multi-well assay plate. Such assay plates are commercially available, for example, from Strategene Corp. (La Jolla, Calif., USA) or Corning Inc. (Acton, Mass., USA) and include, for example, 12-well, 24-well, 48-well, 96-well, 384-well and 1536-well plates.

If desired, cell viability can be determined prior to the assay, for example, using standard techniques including histology, quantitative assessment with radioisotopes, visual observation using a light or scanning electron microscope or a fluorescent microscope. Alternatively, cell viability may be assessed by Fluorescence-Activated Cell Sorting (FACS).

In certain embodiments of the invention, exposing cells to a candidate compound, contacting cells with a candidate compound, or incubating cells with a candidate compound comprises adding the candidate compound to a container (e.g., a well of a multi-well plate) containing cells and incubating the cells in the presence of the candidate compound in a suitable culture medium under conditions and for a period of time such that the effect of the particular candidate compound can be achieved. Exposing cells to a candidate compound to be tested for its effects on the expression of genes of the PLS risk signature is preferably carried out under conditions that allow a known cirrhosis/HCC chemopreventive agent to exert its effects. Such conditions are either well known in the art or may be readily determined, for example, empirically, by one of ordinary skill in the art.

Candidate Compounds

The screening methods of the invention may be used for identifying agents that have the ability to transform the PLS high-risk signature into a PLS low-risk signature. Screening according to the present invention is generally performed with the goal of developing therapeutics useful in the treatment and/or prevention of cirrhosis/HCC, in particular for developing cirrhosis/HCC chemopreventive drugs.

As will be appreciated by those of ordinary skill in the art, any kind of compounds can be tested using the inventive methods. A candidate compound may be a synthetic or natural compound; it may be a single molecule, or a mixture or complex of different molecules. In certain embodiments, a method of screening is used for testing one candidate compound or a few candidate compounds. In other embodiments, a screening method is used for screening collections or libraries of candidate compounds. As used herein, the term "collection" refers to any set of compounds, molecules or agents, while the term "library" refers to any set of compounds, molecules or agents that are structural analogs.

Collections of natural compounds in the form of bacterial, fungal, plant and animal extracts are available from, for example, Pan Laboratories (Bothell, Wash.) or MycoSearch (Durham, N.C.). Libraries of candidate compounds that can be screened using the methods of the present invention may be either prepared or purchased from a number of companies. Synthetic compound libraries are commercially available from, for example, Comgenex (Princeton, N.J.), Brandon Associates (Merrimack, N.H.), Microsource (New Milford, Conn.), and Aldrich (Milwaukee, Wis.). Libraries of candidate compounds have also been developed by and are commercially available from large chemical companies, including, for example, Merck, Glaxo Welcome, Bristol-Meyers-Squibb, Novartis, Monsanto/Searle, and Pharmacia UpJohn. Additionally, natural collections, synthetically produced libraries and compounds are readily modified through conventional chemical, physical, and biochemical means. Chemical libraries are relatively easy to prepare by traditional automated synthesis, PCR, cloning or proprietary synthetic methods (see, for example, S. H. DeWitt et al., Proc. Natl. Acad. Sci. U.S.A. 1993, 90:6909-6913; R. N. Zuckermann et al., J. Med. Chem. 1994, 37: 2678-2685; Carell et al., Angew. Chem. Int. Ed. Engl. 1994, 33: 2059-2060; P. L. Myers, Curr. Opin. Biotechnol. 1997, 8: 701-707). Candidate compounds may also be obtained by any other of the numerous approaches in combinatorial library methods known in the art, including peptoid libraries, spacially addressable parallel solid phase or solution phase libraries; synthetic library methods requiring deconvolution; the "one-bead one-compound" library method; and synthetic library methods using affinity chromatography selection.

Useful agents for the treatment or prevention of cirrhosis/HCC may be found within a large variety of classes of chemicals, including proteins, peptides, peptidomimetics, peptoids, polypeptides, saccharides, steroids, RNA interfering agents, antibodies, ribozymes, antisense oligonucleotides, small molecules and the like. In certain embodiments, the screening methods of the invention are used for identifying compounds or agents that are small molecules. Preferred small organic molecules have a molecule weight of more than about 50 and less than about 2,500 Daltons; such as for example between 600 and 700 Daltons or less than about 350 Daltons.

In certain embodiments, the candidate compounds to be tested using a screening method of the invention have been previously selected by transcriptome-based in silico drug screening using the PLS risk signature exhibited by cells of the cellular model system used.

Effects of the Candidate Compound on the PLS High-Risk Signature

In a screening method according to the invention, the step of determining the effect of a candidate compound on the PLS high-risk gene signature of the liver cells from the cellular model may be performed using any suitable method known in the art that allows to assess the expression profile of genes of the PLS risk gene signature, or of a subset thereof.

Assessing the expression profile of genes of the PLS risk gene signature, or of a subset thereof, is preferably performed on nucleic acid extracts prepared from a sample of liver cells from the cellular model which have been contacted with the candidate compound. For example, RNA may be extracted from the liver cells and analyzed using a method of the invention. Methods of RNA extraction are well known in the art (see, for example, J. Sambrook et al., *"Molecular Cloning: A Laboratory Manual"*, 1989, $2^{nd}$ Ed., Cold Spring Harbour Laboratory Press: New York). Most methods of RNA isolation from cells, bodily fluids or tissues are based on the disruption of the cells or of the tissue in the presence of protein denaturants to quickly and effectively inactivate RNases. Generally, RNA isolation reagents comprise, among other components, guanidium thiocyanate and/or beta-mercaptoethanol, which are known to act as RNase inhibitors. Isolated total RNA may then be further purified from the protein contaminants and concentrated by selective ethanol precipitations, phenol/chloroform extractions followed by isopropanol precipitation (see, for example, Chomczynski and Sacchi, Anal. Biochem., 1987, 162: 156-159) or cesium chloride, lithium chloride or cesium trifluoroacetate gradient centrifugations.

Numerous different and versatile kits can be used to extract RNA (i.e., total RNA or mRNA) from liver cells of the cellular model. Such kits are for example commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), Giagen, Inc. (Valencia, Calif.), and Zymo Research (Irvine, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

After extraction, mRNA may be amplified, and transcribed into cDNA, which can then serve as template for multiple rounds of transcription by the appropriate RNA polymerase. Amplification methods are well known in the art (see, for example, Kimmel and Berger, Methods Enzymol. 1987, 152: 307-316; Sambrook et al., *"Molecular Cloning: A Laboratory Manual"*, 1989, $2^{nd}$ Ed., Cold Spring Harbour Laboratory Press: New York; *"Short Protocols in Molecular Biology"*, Ausubel (Ed.), 2002, $5^{th}$ Ed., John Wiley & Sons; U.S. Pat. Nos. 4,683,195; 4,683,202 and 4,800,159). Reverse transcription reactions may be carried out using non-specific primers, such as an anchored oligo-dT primer, or random sequence primers, or using a target-specific primer complementary to the RNA for each genetic probe being monitored, or using thermostable DNA polymerases (such as avian myeloblastosis virus reverse transcriptase or Moloney murine leukemia virus reverse transcriptase).

In the context of the present invention, assessing the expression profile of genes of the HCC risk gene signature may be performed using any suitable method well known to those skilled in the art. Examples of such methods include, but are not limited to, Southern analysis, Northern analysis, polymerase chain reaction (PCR) (see, for example, U.S. Pat. Nos. 4,683,195; 4,683,202, and 6,040,166; *"PCR Protocols: A Guide to Methods and Applications"*, Innis et al. (Eds.), 1990, Academic Press: New York), reverse transcriptase PCR (RT-PCT) in particular quantitative reverse transcriptase PCR, anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320 308), one-sided PCR (Ohara et al., Proc. Natl. Acad. Sci., 1989, 86: 5673-5677), in situ hybridization, Taqman-based assays (Holland et al., Proc. Natl. Acad. Sci., 1991, 88: 7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like. Other suitable methods include the next generation sequencing technologies which allow for deep sequencing, such as for example RNA-seq (also called Whole Transcriptome Shotgun Sequencing or WTSS) or inferred analyses through L1000 gene expression assays. The results obtained may be analyzed using any suitable method known in the art, such as for example Gene Set Enrichment Analysis (GSEA) (Subramanian et al., PNAS USA, 2005, 102: 15545-1555).

Identification of Cirrhosis/HCC Therapeutic and Chemopreventive Agents

In a screening method of the invention, a candidate compound is identified as useful for the treatment or prevention of cirrhosis/HCC if the candidate compound is able to transform the PLS high-risk signature of liver cells of the cellular model into a PLS low-risk signature. In other words, a candidate compound is identified as useful for the treatment or prevention of cirrhosis/HCC if the candidate compound suppresses the expression of the 73 PLS high-risk genes of Table 1a, or of a subset thereof (for example the 19 PLS high-risk genes of Table 1b), and/or induces the expression of the 113 PLS low-risk genes of Table 1a, or a of a subject thereof (for example the 13 PLS high-risk genes of Table 1b). PLS gene analyses may also be inferred from a genome subset such as L1000.

The term "suppresses the expression of a PLS high-risk gene", as used herein to characterize a candidate compound, is intended to mean that the candidate compound decreases the expression of the PLS high-risk gene to such an extent that the PLS high-risk gene becomes underexpressed (i.e., said PLS high-risk gene is no more overexpressed). The term "induces the expression of a PLS low-risk gene", as used herein to characterize a candidate compound, is intended to mean that the candidate compound increases the expression of the PLS low-risk gene to such extent that the PLS low-risk gene becomes overexpressed (i.e., said PLS low-risk gene is no more underexpressed).

Reproducibility of the results may be tested by incubating liver cells (for example in more than one well of an assay plate) with the same concentration of the same candidate compound. Additionally, since candidate compounds may be effective at different concentrations depending on the nature of the candidate compound and the nature of its mechanism(s) of action, varying concentrations of the candidate compound may be added to different wells containing liver cells. Generally, concentrations from about 1 fM to about 10 mM are used for screening. Preferred screening concentrations are between about 10 pM and about 100 µM. Furthermore, screening different concentrations of a candidate compound according to the methods of the invention allows the $IC_{50}$ value to be determined for that compound.

In certain embodiments, a screening method of the invention further involves the use of one or more negative or positive control compounds. A positive control compound may be any molecule, agent, or drug that is known to transform the PLS high-risk signature of liver cells of the cellular model into a PLS low-risk signature. A negative control compound is any molecule, agent, or drug that is known to have no effect on the PLS high-risk signature of liver cells of the cellular model. In such embodiments, the screening method further comprises a step of comparing the effects of the candidate compound on the PLS high-risk signature to the effects (or absence thereof) of the positive or negative control compound. Such negative and positive control compounds are known in the art (such as for example erlotinib) or may be identified by the methods described herein.

Characterization of Candidate Cirrhosis/HCC Chemopreventive Agents

In another aspect, the invention pertains to the combination of a screening method described herein with one or more additional screening assays. For example, when a screening method of the invention allows to identify a compound as having the ability to transform the PLS high-risk gene signature of cells from a cellular model system into a PLS low-risk gene signature, the ability of the compound can be further confirmed ex vivo, e.g., in animal or human biopsy material or in vivo, e.g., in a whole animal model for cirrhosis/HCC.

Accordingly, it is within the scope of this invention to further use a candidate compound identified by a screening method described herein in an appropriate in vivo animal model and/or in ex vivo animal or human biopsy materials. For example, a compound identified as described herein can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of compounds identified by the above-described screening assay for pre-clinical and clinical assays.

Specific Candidate HCC Chemopreventive Agents

As described in the Examples section below, using the cellular model system of cirrhosis/HCV development and progression, the present Applicants have identified 23 compounds as useful for the treatment or prevention of cirrhosis/HCC, including 9 compounds previously unknown for their cirrhosis/HCC chemoprevention effect. The 24 compounds are AM095, Brefeldin-a, Captopril, Cediranib, Cl-1040, Dilazep, Dorzolamide, Erlotinib, MK-2206, Nizatidine, Orteronel, PD-0325901, Pimarsertib, Pimozide, Pioglitazone, Resveratrol, Rolipram, Selumetinib, TG-101348, Tivozanib, Triamcinolone, iBET, and WDR5-0103. The 13 compounds previously unknown for their HCC chemoprevention or therapeutic effect are Captopril, CI-1040, Dilazep, Dorzolamide, Nizatidine, Orteronel, Pimarsertib, Pioglitazone, Rolipram, TG-101348, C646, iBET, or WDR5-0103, which are provided herein for their use in the treatment and/or prevention of cirrhosis and/or HCC.

Consequently, the present invention encompasses these compounds for the use in the treatment or prevention of cirrhosis/HCC. In particular, the present invention relates to these compounds for their use in the chemoprevention of cirrhosis/HCC.

The present invention also relates to a method of treating or preventing cirrhosis/HCC in a subject, in particular in a human subject, said method comprising a step of: administering to the subject in need thereof an effective amount of one of the above-mentioned compounds.

IV—Pharmaceutical Compositions

A candidate compound identified by a screening method of the present invention as useful for the treatment or prevention of cirrhosis/HCC (e.g., one of the compounds identified Table 4 presented in the Examples section) may be incorporated into pharmaceutical compositions suitable for administration. Such pharmaceutical compositions comprise an effective amount of a candidate compound identified as useful for the treatment and/or prevention of cirrhosis/HCC) and at least one pharmaceutically acceptable carrier. A pharmaceutical composition may further comprise one or more additional biologically active agents.

A pharmaceutical composition according to the invention may be administered in any amount and using any route of administration effective for achieving the desired prophylactic and/or therapeutic effect. The optimal pharmaceutical formulation can be varied depending upon the route of administration and desired dosage. Such formulations may influence the physical state, stability, rate of in vivo release, and rate of in vivo clearance of the administered active ingredient.

The pharmaceutical compositions of the present invention may be formulated in dosage unit form for ease of administration and uniformity of dosage. The expression "unit dosage form", as used herein, refers to a physically discrete unit of a compound identified by a screening method of the present invention as useful for the treatment or prevention of cirrhosis/HCC for the patient to be treated. It will be understood, however, that the total daily dosage of the pharmaceutical compositions will be decided by the attending physician within the scope of sound medical judgement.

Formulation

Injectable preparations, for example, sterile injectable aqueous or oleaginous suspensions may be formulated according to the known art using suitable dispersing or wetting agents, and suspending agents. The sterile injectable preparation may also be a sterile injectable solution, suspension or emulsion in a non-toxic parenterally acceptable diluent or solvent, for example, as a solution in 2,3-butanediol. Among the acceptable vehicles and solvents that may be employed are water, Ringer's solution, U.S.P. and isotonic sodium chloride solution. In addition, sterile, fixed oils are conventionally employed as a solution or suspending medium. For this purpose any bland fixed oil can be employed including synthetic mono- or di-glycerides. Fatty acids such as oleic acid may also be used in the preparation of injectable formulations. Sterile liquid carriers are useful in sterile liquid form compositions for parenteral administration.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Liquid pharmaceutical compositions which are sterile solutions or suspensions can be administered by, for example, intravenous, intramuscular, intraperitoneal or subcutaneous injection. Injection may be via single push or by gradual infusion. Where necessary or desired, the composition may include a local anesthetic to ease pain at the site of injection.

In order to prolong the effect of an active ingredient (i.e., a candidate compound identified as useful for the treatment or prevention of cirrhosis/HCC), it may be desirable to slow the absorption of the ingredient from subcutaneous or intramuscular injection. Delaying absorption of a parenterally administered active ingredient may be accomplished by dissolving or suspending the ingredient in an oil vehicle. Injectable depot forms are made by forming micro-encapsulated matrices of the active ingredient in biodegradable polymers such as polylactide-polyglycolide. Depending upon the ratio of active ingredient to polymer and the nature of the particular polymer employed, the rate of ingredient release can be controlled. Examples of other biodegradable polymers include poly(orthoesters) and poly(anhydrides). Depot injectable formulations can also be prepared by entrapping the active ingredient in liposomes or microemulsions which are compatible with body tissues.

Liquid dosage forms for oral administration include, but are not limited to, pharmaceutically acceptable emulsions, microemulsions, solutions, suspensions, syrups, elixirs, and pressurized compositions. In addition to the active principles, the liquid dosage form may contain inert diluents commonly used in the art such as, for example, water or other solvent, solubilising agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cotton seed, ground nut, corn, germ, olive, castor, and sesame oils), glycerol, tetrahydrofurfuryl alcohol, polyethylene glycols, and fatty acid esters of sorbitan and mixtures thereof. Besides inert diluents, the oral compositions can also include adjuvants such as wetting agents, suspending agents, preservatives, sweetening, flavouring, and perfuming agents, thickening agents, colors, viscosity regulators, stabilizes or osmo-regulators. Examples of suitable liquid carriers for oral administration include water (potentially containing additives as above, e.g., cellulose derivatives, such as sodium carboxymethyl cellulose solution), alcohols (including monohydric alcohols and polyhydric alcohols such as glycols) and their derivatives, and oils (e.g., fractionated coconut oil and arachis oil). For pressurized compositions, the liquid carrier can be halogenated hydrocarbon or other pharmaceutically acceptable propellant.

Solid dosage forms for oral administration include, for example, capsules, tablets, pills, powders, and granules. In such solid dosage forms, an inventive combination may be mixed with at least one inert, physiologically acceptable excipient or carrier such as sodium citrate or dicalcium phosphate and one or more of: (a) fillers or extenders such as starches, lactose, sucrose, glucose, mannital, and silicic acid; (b) binders such as, for example, carboxymethylcellulose, alginates, gelatine, polyvinylpyrrolidone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; absorption accelerators such as quaternary ammonium compounds; (g) wetting agents such as, for example, cetyl alcohol and glycerol monostearate; (h) absorbents such as kaolin and bentonite clay; and (i) lubricants such as talc, calcium stearate, magnesium stearate, solid polyethylene glycols, sodium lauryl sulphate, and mixtures thereof. Other excipients suitable for solid formulations include surface modifying agents such as non-ionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. In the case of capsules, tablets and pills, the dosage form may also comprise buffering agents.

Solid compositions of a similar type may also be employed as fillers in soft and hard-filled gelatine capsules using such excipients as lactose or milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. They may optionally contain opacifying agents and can also be of a composition such that they release the active ingredient(s) only, or preferably, in a certain part of the intestinal tract, optionally, in a delaying manner. Examples of embedding compositions which can be used include polymeric substances and waxes.

In certain embodiments, it may be desirable to administer a pharmaceutical composition locally to an area in need of treatment (e.g., the liver). This may be achieved, for example, and not by way of limitation, by local infusion during surgery (e.g., liver transplant), topical application, by injection, by means of a catheter, by means of suppository, or by means of a skin patch or stent or other implant.

For topical administration, the composition is preferably formulated as a gel, an ointment, a lotion, or a cream which can include carriers such as water, glycerol, alcohol, propylene glycol, fatty alcohols, triglycerides, fatty acid esters, or mineral oil. Other topical carriers include liquid petroleum, isopropyl palmitate, polyethylene glycol, ethanol (95%), polyoxyethylenemonolaurat (5%) in water, or sodium lauryl sulphate (5%) in water. Other materials such as antioxidants, humectants, viscosity stabilizers, and similar agents may be added as necessary.

A pharmaceutical composition may alternatively be disposed within transdermal devices placed upon, in, or under the skin. Such devices include patches, implants, and injections which release the active ingredient by either passive or active release mechanisms. Transdermal administrations include all administration across the surface of the body and the inner linings of bodily passage including epithelial and mucosal tissues. Such administrations may be carried out using the present compositions in lotions, creams, foams, patches, suspensions, solutions, and suppositories (rectal and vaginal).

Transdermal administration may be accomplished through the use of a transdermal patch containing an active ingredient (i.e., a compound identified as useful for the treatment or prevention of cirrhosis/HCC by a screening method described herein) and a carrier that is non-toxic to the skin, and allows the delivery of the ingredient for systemic absorption into the bloodstream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may be suitable. A variety of occlusive devices may be used to release the active ingredient into the bloodstream such as a semi-permeable membrane covering a reservoir containing the active ingredient with or without a carrier, or a matrix containing the active ingredient.

Suppository formulations may be made from traditional materials, including cocoa butter, with or without the addition of waxes to alter the suppository's melting point, and glycerine. Water soluble suppository bases, such as polyethylene glycols of various molecular weights, may also be used.

Materials and methods for producing various formulations are known in the art and may be adapted for practicing the subject invention. Suitable formulations for the delivery of antibodies can be found, for example, in "*Remington's Pharmaceutical Sciences*", E. W. Martin, 18$^{th}$ Ed., 1990, Mack Publishing Co.: Easton, Pa.

Additional Biologically Active Agents

In certain embodiments, a compound identified as useful for the treatment or prevention of cirrhosis/HCC by a screening method described herein is the only active ingredient in a pharmaceutical composition of the present invention. In other embodiments, the pharmaceutical composition further comprises one or more biologically active agents.

As used herein, the term "biologically active agent" refers to any molecule or compound whose presence in a pharmaceutical composition of the invention is beneficial to the subject receiving the composition. As will be acknowledged by one skilled in the art, biologically active agents suitable for use in the practice of the present invention may be found in a wide variety of families of bioactive molecules and compounds. Examples of suitable biologically active agents include, but are not limited to, therapeutic agents such as anti-viral agents, anti-inflammatory agents, immunosuppressive or immunomodulatory agents, analgesics, anti-apoptotic agents, antimicrobial agents, antibacterial agents, antibiotics, antioxidants, antiseptic agents, and combinations thereof.

In such pharmaceutical compositions, the cirrhosis/HCC chemopreventive agent and the one or more additional biologically active agent(s) may be combined in one or more preparations for simultaneous, separate or sequential administration of the different components. More specifically, a cirrhosis/HCC chemopreventive agent may be formulated in such a way that the cirrhosis/HCC chemopreventive agent and additional biologically active agent(s) can be administered together or independently from one another. For example, a cirrhosis/HCC chemopreventive agent and an additional biological active agent can be formulated together in a single composition. Alternatively, they may be maintained (e.g., in different compositions and/or containers) and administered separately.

Administration

A cirrhosis/HCC chemopreventive agent identified by a screening method described herein, or a pharmaceutical composition thereof, can be administered to a subject in need thereof by any suitable route. Various delivery systems are known and can be used, including tablets, capsules, injectable solutions, encapsulation in liposomes, microparticles, microcapsules, etc. Methods of administration include, but are not limited to, dermal, intradermal, intramuscular, intraperitoneal, intralesional, intravenous, subcutaneous, intranasal, pulmonary, epidural, ocular, and oral routes. A cirrhosis/HCC chemopreventive/therapeutic agent, or a pharmaceutical composition thereof, may be administered by any convenient or other appropriate route, for example, by infusion or bolus injection, by absorption through epithelial or mucocutaneous linings (e.g., oral, mucosa, rectal and intestinal mucosa, etc). Administration can be systemic or local. Parenteral administration may be preferentially directed to the patient's liver, such as by catheterization to hepatic arteries or into a bile duct. As will be appreciated by those of ordinary skill in the art, in embodiments where the cirrhosis/HCC chemopreventive agent and additional biologically active agent(s) are administered sequentially (i.e., at different times or separately but at substantially the same time), the cirrhosis/HCC chemopreventive/therapeutic agent and additional biologically active agent(s) may be administered by the same route (e.g., intravenously) or by different routes (e.g., orally and intravenously).

Dosage

Administration of a cirrhosis/HCC chemopreventive/ therapeutic agent, or a pharmaceutical composition thereof, will be in a dosage such that the amount delivered is effective for the intended purpose. The route of administration, formulation and dosage administered will depend upon the therapeutic effect desired, the severity of the condition to be treated if already present, the presence of any infection, the age, sex, weight, and general health condition of the patient as well as upon the potency, bioavailability, and in vivo half-life of the cirrhosis/HCC chemopreventive/therapeutic agent used, the use (or not) of concomitant therapies, and other clinical factors. These factors are readily determinable by the attending physician in the course of the therapy. Alternatively or additionally, the dosage to be administered can be determined from studies using animal models (e.g., chimpanzee or mice). Adjusting the dose to achieve maximal efficacy based on these or other methods are well known in the art and are within the capabilities of trained physicians.

A treatment according to the present invention may consist of a single dose or multiple doses. Thus, administration of a cirrhosis/HCC chemopreventive/therapeutic agent, or pharmaceutical composition thereof, may be constant for a certain period of time or periodic and at specific intervals, e.g., hourly, daily, weekly (or at some other multiple day interval), monthly, yearly (e.g., in a time release form). Alternatively, the delivery may occur at multiple times during a given time period, e.g., two or more times per week; two or more times per month, and the like. The delivery may be continuous delivery for a period of time, e.g., intravenous delivery.

In general, the amount of cirrhosis/HCC chemopreventive/therapeutic agent, or pharmaceutical composition thereof, administered will preferably be in the range of about 1 ng/kg to about 100 mg/kg body weight of the subject, for example, between about 100 ng/kg and about 50 mg/kg body weight of the subject; or between about 1 µg/kg and about 10 mg/kg body weight of the subject, or between about 100 µg/kg and about 1 mg/kg body weight of the subject.

V—Uses of the Non-Hepatic Cancer Cellular Model

As indicated above, the Applicants have shown that non-hepatic cancer cell lines, including (Caco-2/TC7) and cervical (HeLa) cells can be used as a model to express the Prognostic Liver Signature (PLS) following ethanol exposure. In other words, the Prognostic Liver Signature has been identified as a more general signature of cancer development and progression.

The non-hepatic cancer cell lines that can be used in a method according to the invention may be any non-hepatic cancer cell line known in the art. For example, the cell lines may be from bone cancer, bladder cancer, brain cancer, breast cancer, cancer of the urinary tract, cervical cancer, colon cancer, endometrium cancer, esophageal cancer, eye cancer, gastric cancer, head and neck cancer, lung cancer, lymphoma and leukemia, mouth cancer, ovarian cancer, pancreatic cancer, pituitary cancer, prostate cancer, rectal cancer, renal cancer, stomach cancer, testicular cancer, thyroid cancer, throat cancer, or uterine cancer.

A cell model obtained, using a method as described herein, from non-hepatic cancer cells may be used for identifying agents useful in the treatment and/or prevention of a non-hepatic cancer (such as those listed above).

The invention will be further illustrated by the following figures and examples. However, these examples and figures should not be interpreted in any way as limiting the scope of the present invention.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

In the Examples below, the Prognostic Liver Signature (PLS) is described as a HCC risk signature because HCC is the specific focus of the study, demonstrating an application of PLS (HCC chemoprevention).

Example 1

Materials and Methods

Human Subjects. Human material, including serum from patients with chronic HBV or HDV infection treated at the Strasbourg University Hospitals (Strasbourg, France), was obtained after informed consent from all subjects. Human liver tissues were obtained from HCC patients undergoing liver resection after informed consent from all patients for de-identified use at the Mount Sinai Hospital (New York, N.Y., USA). The protocols were approved by the local Ethics Committee for the University Strasbourg Hospitals and Mount Sinai Hospital, respectively.

Reagents and Antibodies. Absolute ethanol was purchased from Thermo Fisher Scientific (Waltham, Mass., USA); erlotinib from LC Laboratories (Woburn, Mass., USA); interferon-alpha 2a from Roche (Penzberg, Germany); pioglitazone, primidone, triamcinolone, pimozide, dilazep HCl2, dorzolamide and dimethyl sulfoxide (DMSO) from Sigma-Aldrich (St. Louis, Mo., USA); Fr180204 from Merk (Billerica, Mass., USA); oxetacaine and pralidoxime from Santa Cruz (Dallas, Tex., USA); captopril, selumetinib, MK-2206, nizatidine, ramipril, clomifene citrate, PD-0325901, pimasertib, tivozanib, brefeldin-a, rolipram, TG-101348, CI-10140, isoliquiritigenin, tolnaftate, cediranib, orteronel, resveratrol and tipifarnib from Selleckchem (Houston, Tex., USA). AM095 was kindly provided by Amira Pharmaceuticals (San Francisco, Calif., USA). Daclatasvir and sofosbuvir were synthesized by Acme Biosciences (Palo Alto, Calif., USA). iBET, WDR5-0103, SAHA were purchased from Sigma-Aldrich. C646, CTK7A and MM102 were purchased from Merck Millipore. The Human Phospho-RTK Array kit and the Proteome Profiler Human Phospho-kinase Array kit were obtained from R&D Systems (Minneapolis, Minn., USA). The ECL reagent and Hyperfilms were purchased from GE Healthcare (Cleveland, Ohio, USA). HCV E2-specific AP33 antibody (mouse) has previously been described (Fofana et al., Gastroenterology, 2010, 139: 953-964). Human IgG containing antibodies targeting the hepatitis delta Ag (HDAg) were purified from the serum of a HDV-infected patient using MAbTrap Kit (GE Healthcare, Cleveland, Ohio, USA) according to manufacturer's instructions. Hepatitis B surface antigen (HBsAg)-specific monoclonal antibody (NCL-HBsAg-2, clone 1044/341) was obtained from Leica Biosystems (Wetzlar, Germany); Alexa Fluor® 647 anti-mouse IgG (goat) and Alexa Fluor® 647 anti-human IgG (goat) from Jackson ImmunoResearch (West Grove, Pa., USA), and DAPI from Life Technologies (Carlsbad, Calif., USA).

Cell Lines. Hepatocellular carcinoma-derived Huh7.5.1 (Zhong et al., PNAS USA, 2005, 12: 9294-9299) and HepAD38 (Ladner et al., Antimicrob. Agents Chemother., 1997, 41: 1715-1720), hepatoblastoma-derived HepG2 (Lupberger et al., Nat. Med., 2011, 17: 589-595) and human stellate LX-2 cells (Xu et al., Gut, 2005, 54: 142-151) have been described. All cell lines were certified mycoplasma-free. For HDV infection and HBV infection, Huh7.5.1 and HepG2 cells were stably transduced using human NTCP-expressing vesicular stomatitis virus pseudoparticles (VSVpp) (GeneCopoeia, Rockville, Md., USA). NTCP-overexpres sing Huh7.5.1-NTCP or HepG2-NTCP cells were selected using puromycin as previously described (Ni et al., Gastroenterology, 2014, 146: 1070-1083; Yan et al., eLife, 2012, e00049; Wakita et al., Nat. Med., 2005, 11: 791-796). For proliferation arrest and differentiation (Huh7.5.1$^{dif}$ cells), $2.5.10^4$ to $3.10^4$ Huh7.5.1 cells were cultured in Dulbecco's Modified Eagle Medium (DMEM) containing 1% DMSO. For co-culture experiments, $2.5.10^4$ Huh7.5.1 cells were seeded in a P6-well format together with different percentages of LX-2 hepatic stellate cells (0%, 5%, 10% and 20% of total cells), and maintained in 1% DMSO-complemented medium.

HCV Infection of Huh7.5.1$^{dif}$ cells. Cell culture-derived HCVcc Jc1 (genotype 2a/2a) (Pietschmann et al., PNAS USA, 2006, 103: 7408-7413) were generated in Huh7.5.1 cells as previously described (Wakita et al., Nat. Med., 2005, 11: 791-796). HCV Jc1E2$^{FLAG}$ was purified using anti-FLAG M2 affinity gel (Sigma-Aldrich, St.Louis, Mo., USA) as described (Merz et al., J. Biol. Chem., 2011, 286: 3018-3032). HCVcc infectivity was determined by calculating the 50% tissue culture infectious doses (TCID$_{50}$) as previously described (Lindenbach et al., Science, 2005, 309: 623-626). Huh7.5.1$^{dif}$ cells were infected with HCV Jc1 or HCV Jc1E2$^{FLAG}$. Cell culture supernatants from mock-electroporated cells or 100 µg/mL of FLAG peptide were used for control experiments. HCV infection was assessed by qRT-PCR of intracellular HCV RNA (Xiao et al., PLoS Pathog., 2014, 10: e1004128) as well as immunostaining using HCV E2-specific AP33 antibody as previously described (Krieger et al., Hepatology, 2010, 51: 1144-1157). Seven days after HCV Jc1 infection, Huh7.5.1$^{dif}$ cells were incubated for three days with either 10 IU/mL interferon-alpha 2a, a combination of 1 nM daclatasvir and 1 µM sofosbuvir, or erlotinib (0.1 µM), tipifarnib (10 µM), Fr180204 (10 µM).

High-Throughput Screen for Chemoprevention Drug Discovery. Huh7.5.1$^{dif.}$ cells were seeded in P96-well format and maintained in 1% DMSO-complemented medium. Cells were infected with HCV Jc1 or cell culture supernatant from mock-electroporated cells for non-infected control wells as described above. Seven days after infection, cells were incubated with either AM095 (1 µM), brefeldin-a (0.1 µM), captopril (1 µM or 5 µM), cediranib (0.5 µM), CI-1040 (1 µM), clomifene citrate (1 µM), dilazep HCl2 (1 µM), dorzolamide (10 µM), isoliquiritigenin (10 µM), MK-2206 (1 µM), nizatidine (10 µM), orteronel (40 µM), oxetacaine (10 µM), PD-0325901 (10 nM), pimasertib (0.5 µM), pimozide (1 µM), pioglitazone (1 µM), pralidoxime (10 µM), primidone (10 µM), ramipril (10 µM), resveratrol (10 µM), rolipram (10 µM), selumetinib (0.5 µM), TG-101348 (0.1 µM), tivozanib (0.5 µM), tolnaftate (10 µM) or triamcinolone (58 nM). After three days of treatment, cells were washed with PBS, lysed with 5 μl of iScript™ RT-qPCR Sample Preparation Reagent (Bio-rad, Marne-la-Coquette, France) and subjected to NCOUNTER Digital Analyzer system (NanoString) to evaluate the 32-gene HCC risk signature (see Table 1b) (King et al., Gut, 2014, e114747). Toxicity was analyzed in parallel using Presto Blue reagent according to manufacturer's recommendations (Life Technologies, Carlsbad, Calif., USA).

HDV Infection of Huh7.5.1$^{dif}$-NTCP Cells. Recombinant HDV was produced as previously described (Verrier et al., Hepatology, 2015, 63: 35-48). NTCP-overexpressing Huh7.5.1$^{dif}$ cells were infected with recombinant HDV in presence of 4% polyethylene glycol and cultured for 10 days in 2% DMSO-complemented primary hepatocyte maintenance medium (PMM) as previously described (Verrier et al., Hepatology, 2015, 63: 35-48; Ni et al., Gastroenterology, 2014, 146: 1070-1083; and Yan et al., eLife, 2012, e00049). HDV infection was assessed by qRT-PCR of HDV RNA and immunodetection of HDAg using serum-derived anti-HDAg antibodies as previously described (Verrier et al., Hepatology, 2015, 63: 35-48).

HBV Infection of HepG2*-NTCP Cells. HBV (genotype D) was purified from the serum of a HBV carrier (Habersetzer et al., Liver Int., 2015, 35: 130-139). Viral particles were concentrated using ultracentrifugation by pelleting over a 30% sucrose cushion with subsequent gradient centrifugation using a 10-45% iodixanol density gradient similar as described (Verrier et al., Hepatology, 2015, 63: 35-48; Abdul et al., PLoS One, 2012, 7: e48721). HepG2-NTCP cells were then infected with purified HBV or control preparation in the presence of 4% polyethylene glycol and maintained in culture for additional 10 days in 2% DMSO-complemented PMM as previously described (Verrier et al., Hepatology, 2015, 63: 35-48). HBV infection was assessed by qRT-PCR quantification of HBV pregenomic RNA in cell lysates as well as by immunodetection of HBsAg using HBsAg-specific monoclonal antibody (NCL-HBsAg-2, clone 1044/341) as previously described (Verrier et al., Hepatology, 2015, 63: 35-48).

Ethanol Treatment of Huh7.5.1$^{dif}$ Cells. Huh7.5.1$^{dif}$ cells were incubated in the presence or absence of ethanol (20 or 40 mM) and fresh medium containing ethanol was replenished every day (Ye et al., *Drug Alcohol Depend.*, 2010, 112: 107-116).

Liver Slices. Fresh liver tissue sections (300 μm-thick) were prepared from surgically resected fibrotic livers from HCC patients using Krumdieck Tissue Slicer MD6000 (Alabama Research and Development, Munford, Ala., USA). The tissues were cultured with erlotinib (5 μM) or pioglitazone (10 μM) for 48 hours and harvested for gene expression analysis.

Transcriptional Analyses. Liver cells were lysed in TRI-reagent (Molecular Research Center; Cincinnati, Ohio, USA), and RNA was purified using Direct-zol RNA Mini-Prep (Zymo Research, Irvine, Calif., USA) according to manufacturer's instructions. RNA quantity and RNA quality were assessed using NanoDrop (Thermo Scientific, Waltham, Mass., USA) and Bioanalyzer 2100 (Illumina, San Diego, Calif., USA) with a quality cut-off of RNA Integrity Number >8. RNA from HDV- and HBV-infected liver cells as well as from human liver tissue was purified using the RNeasy kit (Qiagen, Hilden, Germany). Gene expression profiling was performed using 250-500 ng total RNA by using either NCOUNTER Digital Analyzer system (NanoString) or the HumanHT-12 beadarray (Illumina, San Diego, Calif., USA). HCC high risk gene expression was analyzed by qRT-PCR using specific TaqMan Gene Expression Assays (Life Technologies, Carlsbad, Calif., USA) or the ANXA3 and GPX2 primer sets previously described (Pan et al., Stem Cells, 2015, 33: 354-366 and Brault et al., Gut, 2014, 65: 44-54, respectively). The expression of GAPDH mRNA was analyzed as a reference gene using a specific TaqMan Gene Expression Assay (Life Technologies, Carlsbad, Calif., USA) or the RT2 qPCR Primer Assay (Qiagen, Hilden, Germany). Relative gene expression level was calculated by the $\Delta\Delta$Ct method as previously described (Schmittgen et al., Nat. Protoc., 2008, 3: 1101-1108).

Proteomic Analyses. For proteomic analyses, Huh7.5.1$^{dif}$ cells that had undergone DMSO-mediated differentiation, were infected with HCV Jc1E2$^{FLAG}$ (TCID$_{50}$=10$^7$/mL) as described above. On day 7, receptor tyrosine kinase (RTK) phosphorylation was assessed in cell lysates using the Human Phospho-RTK Array Kit as previously described (Lupberger et al., Nat. Med., 2011, 17: 589-595; and Zona et al., Cell Host Microbe, 2013, 13: 302-313). The effect of MAPK inhibitors on signaling was confirmed using the Proteome Profiler Human Phospho-kinase Array according to manufacturer's instructions (R&D Systems). Amounts of phospho-proteins were assessed using a horseradish peroxidase-conjugated pan-phospho-tyrosine-specific antibody (R&D Systems, Minneapolis, Minn., USA) followed by chemiluminescence detection (GE Healthcare, Cleveland, Ohio, USA) according to manufacturer's instructions. The relative dot-blot density of the phosphorylated proteins in HCV Jc1E2$^{FLAG}$ infected samples compared to non-infected controls was quantified using Image J software (NIH) by elliptical selection of individual dots and measuring standard deviation and integrated density.

Metabolomics. Analysis of polar metabolites was performed in Huh7.5.1$^{dif}$ cells infected with HCV Jc1E2$^{FLAG}$ (TCID$_{50}$=10$^5$/mL). On day 7, intra- and extra-cellular metabolites were extracted from cell lysates and supernatants, respectively, and further analyzed by mass spectrometry as previously described (Nicolay et al., Genes Dev., 2013, 27: 182-196; Xia et al., Nucleic Acids Res., 2009, 37: W652-660).

Selection of Compounds for the Molecular Signature-Based Drug Screening. Transcriptome-based in silico drug screening was performed using the HCC risk signature as a query in the chemogenomics database connectivity map (cmap, webite: broadinstitute.org/cmap) and the LINCS database (website: lincscloud.org) as previously described (Lamb et al., Science, 2006, 313: 1929-1935). Cmap-predicted compounds with a negative enrichment score and a p-value<0.05, and LINCS-predicted compounds with connectivity score <−90 were further selected with respect to their approval in clinical trials according to the website: clinicaltrials.gov. Compounds that have been formally licensed for clinical use, compounds currently being evaluated in phase 3-4 clinical trials and compounds with a putative relevance for HCC currently being evaluated in phase 2 clinical trials were selected for assessment in the cell-based model. Known carcinogens, antibiotics and compounds associated with severe liver toxicity according to LiverTox database (website: livertox.nlm.nih.gov) were discarded.

Bioinformatics. Induction or suppression of HCC risk signature in HumanHT-12 beadarray (Illumina, San Diego, Calif., USA) data was determined as previously reported by using Nearest Template Prediction algorithm and Gene Set Enrichment Analysis (GSEA), implemented in GenePattern genomic analysis toolkits (Subramanian et al., PNAS USA, 2005, 102: 15545-15550; Hoshida, PLoS One, 2010, 5: e15543; Reich et al., Nat. Genet., 2006, 38: 500-501).

Molecular pathway deregulations were determined in Molecular Signature Database (MSigDB, ver.4.0) (Liberzon et al., *Bioinformatics*, 2011, 27: 1739-1740) using GSEA (Subramanian et al., PNAS USA, 2005, 102: 15545-15550). Liver- or HCC-specific gene signatures were defined by comparing global transcriptome profiles of 82 human liver tissues and 118 HCC tumor tissues from Applicants previous studies (Hoshida et al., N. Engl. J. Med., 2008, 359: 1995-2004; Hoshida et al., Cancer Res., 2009, 69: 7385-7392) using random permutation-based t-test implemented in GenePattern. Genome-wide transcriptome profiles in Huh7.5.1$^{dif}$ cells were compared to previously published transcriptomic data in naïve Huh7.5 cells (NCBI Gene Expression Omnibus database, accession number: GSE62546). Comparison between the cell-based systems and clinical datasets was performed using Subclass Mapping algorithm (Hoshida et al., PLoS One, 2007, 2: e1195) implemented in GenePattern. Co-regulated gene networks and enriched molecular pathways in the HCC high-risk genes common to multiple HCC etiologies were determined using Ingenuity Pathway Analysis (website: ingenuity.com). False discovery rate (FDR) <0.05 or Bonferroni-corrected p<0.05 were regarded as statistically significant. All genomic datasets used for this study are available at NCBI Gene Expression Omnibus database (website: ncbi.nlm.nih.gov/geo, accession number: GSE66843).

Results

Induction of the HCC risk signature in a human liver cell-based system by HCV infection. Since chronic hepatitis C has been described as a major inducer of the HCC high risk signature in patients (Hoshida et al., N. Engl. J. Med., 2008, 359: 1995-2004), the Applicants first explored HCV infectious cell culture systems to model the clinical signature. Taking advantage of a previous observation that DMSO differentiation of Huh7-derived liver cells results in induction of a hepatocyte-like in long term culture (Bauhofer et al., Gastroenterology, 2012, 143: 429-438), the Applicants established a model system that allows to differentiate Huh7.5.1 cells into hepatocyte-like cells within 10 days (see FIG. 1a). They then infected the hepatocyte-like Huh7.5.1$^{dif.}$ cells with HCV strain Jc1 (Pietschmann et al., PNAS USA, 2006, 103: 7408-7413; Mailly et al., Nat. Biotechnol., 2015, 33: 549-554) (see FIG. 1a-b). Strickingly, they discovered that persistent HCV infection of the differentiated liver cells resulted in robust induction of a HCC risk 186-gene signature (see Table 1) using an FDA-approved diagnostic platform, NCOUNTER assay (NanoString) (King et al., Gut, 2015, 64: 1296-1302) (see FIG. 1c).

TABLE 1a

The PLS/HCC risk 186-gene signature. The HCC risk 186-gene signature comprises 73 high risk genes and 103 low risk genes.

| Gene ID | Gene Symbol | Gene ID | Gene Symbol |
|---|---|---|---|
| PLS/HCC High Risk Genes ||||
| 2488 | FSHB | 3855 | KRT7 |
| 6456 | SH3GL2 | 5271 | SERPINB8 |
| 23029 | RBM34 | 4791 | NFKB2 |
| 23397 | NCAPH | 165 | AEBP1 |
| 1950 | EGF | 7041 | TGFB1I1 |
| 7204 | TRIO | 2013 | EMP2 |
| 1293 | COL6A3 | 596 | BCL2 |
| 3983 | ABLIM1 | 5698 | PSMB9 |
| 3680 | ITGA9 | 10097 | ACTR2 |
| 4922 | NTS | 780 | DDR1 |
| 5055 | SERPINB2 | 6541 | SLC7A1 |
| 4316 | MMP7 | 5420 | PODXL |

TABLE 1a-continued

The PLS/HCC risk 186-gene signature. The HCC risk 186-gene signature comprises 73 high risk genes and 103 low risk genes.

| Gene ID | Gene Symbol | Gene ID | Gene Symbol |
|---|---|---|---|
| 5593 | PRKG2 | 1307 | COL16A1 |
| 9170 | EDG4 | 10437 | IFI30 |
| 4843 | NOS2A | 9852 | EPM2AIP1 |
| 2043 | EPHA4 | 301 | ANXA1 |
| 6672 | SP100 | 6366 | CCL21 |
| 2326 | FMO1 | 22856 | CHSY1 |
| 2877 | GPX2 | 162 | AP1B1 |
| 496 | ATP4B | 7004 | TEAD4 |
| 8870 | IER3 | 54898 | ELOVL2 |
| 7456 | WIPF1 | 6925 | TCF4 |
| 3489 | IGFBP6 | 9819 | TSC22D2 |
| 1501 | CTNND2 | 1847 | DUSP5 |
| 2200 | FBN1 | 8030 | CCDC6 |
| 2629 | GBA | 962 | CD48 |
| 22858 | ICK | 10188 | TNK2 |
| 10523 | CHERP | 1601 | DAB2 |
| 9734 | HDAC9 | 4017 | LOXL2 |
| 51406 | NOL7 | 6035 | RNASE1 |
| 8826 | IQGAP1 | 4026 | LPP |
| 120 | ADD3 | 7852 | CXCR4 |
| 306 | ANXA3 | 6586 | SLIT3 |
| 10362 | HMG20B | 11259 | FILIP1L |
| 6558 | SLC12A2 | 6363 | CCL19 |
| 1282 | COL4A1 | 11214 | AKAP13 |
| 1359 | CPA3 | | |
| PLS/HCC Low Risk Genes ||||
| 223 | ALDH9A1 | 27072 | VPS41 |
| 7276 | TTR | 2642 | GCGR |
| 6018 | RLF | 10694 | CCT8 |
| 3612 | IMPA1 | 25874 | BRP44 |
| 5207 | PFKFB1 | 2868 | GRK4 |
| 6296 | ACSM3 | 3336 | HSPE1 |
| 151 | ADRA2B | 79731 | NARS2 |
| 5771 | PTPN2 | 667 | DST |
| 5691 | PSMB3 | 27032 | ATP2C1 |
| 5502 | PPP1R1A | 10327 | AKR1A1 |
| 27346 | TMEM97 | 2010 | EMD |
| 5313 | PKLR | 799 | CALCR |
| 9252 | RPS6KA5 | 22839 | DLGAP4 |
| 1528 | CYB5A | 6240 | RRM1 |
| 6447 | SCG5 | 29937 | NENF |
| 25828 | TXN2 | 29887 | SNX10 |
| 5340 | PLG | 5372 | PMM1 |
| 6309 | SC5DL | 6999 | TDO2 |
| 367 | AR | 2944 | GSTM1 |
| 3479 | IGF1 | 6721 | SREBF2 |
| 8802 | SUCLG1 | 26469 | PTPN18 |
| 23498 | HAAO | 27163 | ASAHL |
| 735 | C9 | 5336 | PLCG2 |
| 9013 | TAF1C | 3760 | KCNJ3 |
| 1371 | CPOX | 5833 | PCYT2 |
| 7507 | XPA | 2705 | GJB1 |
| 3026 | HABP2 | 7108 | TM7SF2 |
| 2690 | GHR | 8991 | SELENBP1 |
| 5105 | PCK1 | 316 | AOX1 |
| 6718 | AKR1D1 | 10444 | ZER1 |
| 128 | ADH5 | 130 | ADH6 |
| 16 | AARS | 2956 | MSH6 |
| 732 | C8B | 8671 | SLC4A4 |
| 51237 | MGC29506 | 9097 | USP14 |
| 10159 | ATP6AP2 | 727 | C5 |
| 9732 | DOCK4 | 5893 | RAD52 |
| 5627 | PROS1 | 116496 | FAM129A |
| 7709 | ZBTB17 | 10458 | BAIAP2 |
| 1603 | DAD1 | 6744 | SSFA2 |
| 1678 | TIMM8A | 5446 | PON3 |
| 3155 | HMGCL | 2646 | GCKR |
| 725 | C4BPB | 1385 | CREB1 |
| 7189 | TRAF6 | 23316 | CUTL2 |
| 1967 | EIF2B1 | 6427 | SFRS2 |
| 3990 | LIPC | 3156 | HMGCR |
| 10026 | PIGK | 2677 | GGCX |
| 80344 | WDR23 | 1555 | CYP2B6 |
| 5982 | RFC2 | 7739 | ZNF185 |

TABLE 1a-continued

The PLS/HCC risk 186-gene signature. The HCC risk 186-gene signature comprises 73 high risk genes and 103 low risk genes.

| Gene ID | Gene Symbol | Gene ID | Gene Symbol |
|---|---|---|---|
| 2915 | GRM5 | 378 | ARF4 |
| 6391 | SDHC | 10965 | ACOT2 |
| 2073 | ERCC5 | 513 | ATP5D |
| 2158 | F9 | 1369 | CPN1 |
| 157567 | ANKRD46 | 5331 | PLCB3 |
| 417 | ART1 | 3642 | INSM1 |
| 1486 | CTBS | 5442 | POLRMT |
| 2542 | SLC37A4 | 11145 | HRASLS3 |
| 211 | ALAS1 | | |

TABLE 1b

The PLS/HCC risk 32-gene signature. The HCC risk 32-gene signature comprises 19 high risk genes and 13 low risk genes.

| PLS/HCC High Risk Genes | | PLS/HCC Low Risk Genes | |
|---|---|---|---|
| Gene ID | Gene Symbol | Gene ID | Gene Symbol |
| 2488 | FSHB | 223 | ALDH9A1 |
| 6456 | SH3GL2 | 7276 | TTR |
| 23029 | RBM34 | 6018 | RLF |
| 23397 | NCAPH | 3612 | IMPA1 |
| 1950 | EGF | 5207 | PFKFB1 |
| 7204 | TRIO | 6296 | ACSM3 |
| 1293 | COL6A3 | 151 | ADRA2B |
| 3983 | ABLIM1 | 5771 | PTPN2 |
| 3680 | ITGA9 | 5691 | PSMB3 |
| 4922 | NTS | 5502 | PPP1R1A |
| 5055 | SERPINB2 | 27346 | TMEM97 |
| 4316 | MMP7 | 5313 | PKLR |
| 5593 | PRKG2 | 9252 | RPS6KA5 |
| 9170 | EDG4 | | |
| 4843 | NOS2A | | |
| 2043 | EPHA4 | | |
| 6672 | SP100 | | |
| 2326 | FMO1 | | |
| 2877 | GPX2 | | |

Induction of the signature was found to be dose-dependent (with a threshold viral load of $10^4$ tissue culture infectious dose 50/mL—see FIG. 1d) and time-dependent (with full development from day 7 post-infection—data not shown). Infection using highly purified FLAG-tagged virus (HCV Jc1E2$^{FLAG}$) (Merz et al., J. Biol. Chem., 2011, 286: 3018-3032) showed a similar induction of the HCC risk signature (see FIG. 1d), confirming that the clinical signature was triggered by HCV. Interferon-alpha 2a (IFNα-2a) or direct-acting antiviral (DAA) treatment for HCV, which decreased viral load about 100-fold, resulted in partial suppression of the HCC high-risk gene expression and restoration of HCC low-risk gene expression (see FIG. 1d), corroborating the causal link between persistent viral infection and induction of the HCC risk signature.

Figure 2:
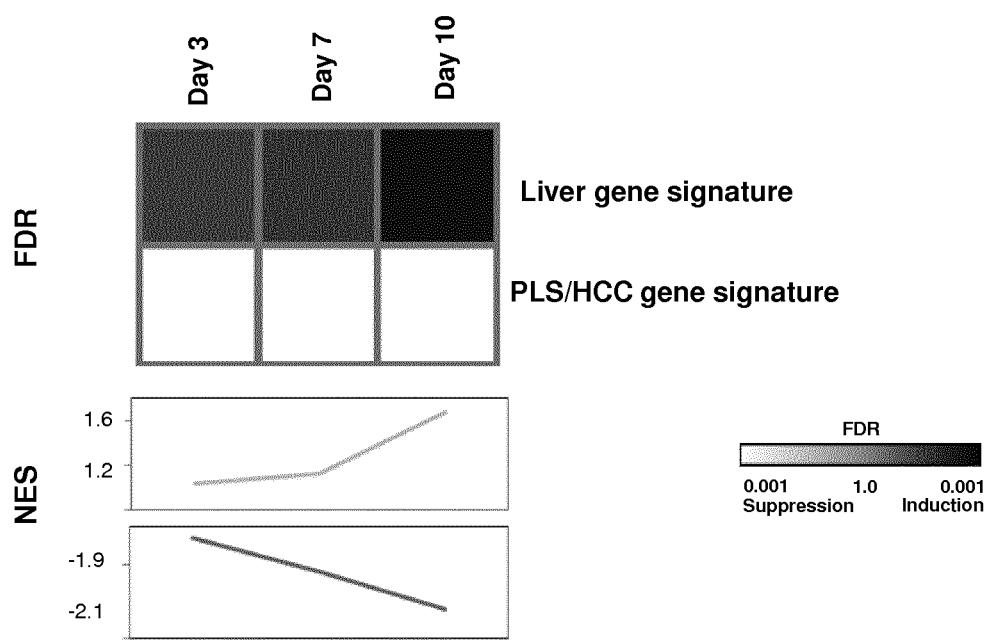
FIG. 2. Time-course of molecular pathway modulation during DMSO-induced differentiation of Huh7.5.1 into hepatocyte-like cells. Naïve Huh7.5.1 cells were differentiated with DMSO and RNA was isolated and analyzed as described in FIG. 1a. DMSO-differentiation induces a hepatocyte-like phenotype in Huh7.5.1$^{dif}$ cells as shown by a gradual shift of an HCC tissue-specific gene signature to a non-cancer liver tissue-specific gene signature over time. Modulation of 482 genes specifically over-expressed in human non-malignant liver tissue (liver tissue-specific gene signature) or 1,106 genes specifically over-expressed in HCC tissues (HCC tissue-specific gene signature) defined in genome-wide transcriptome profiles of 200 clinical specimens (see Materials and Methods) was assessed in Huh7.5.1$^{dif}$ cells. Genome-wide transcriptome profiles in Huh7.5.1$^{dif}$ cells were compared to previously published transcriptomic data in naïve Huh7.5 cells. In the heatmap, dense back indicates significant induction, white indicates significant suppression. FDR: false discovery rate; NES: normalized enrichment score. The results shown are representative of one experiment performed in triplicate.

Genome-wide transcriptome profiling of HCV non-infected cells confirmed hepatocyte-like differentiation of Huh7.5.1 cells by DMSO: the Applicants observed a striking induction of a liver tissue-specific gene signature and suppression of HCC tissue-specific gene signature using Gene Set Enrichment Analysis (GSEA) (Subramanian et al., PNAS USA, 2005, 102: 15545-15550) (see FIG. 2). These findings demonstrate that cellular differentiation in non-infected cells results in a shift of the global transcriptome pattern from a malignant to a non-malignant hepatocyte-like profile. A human liver cell system has thus been established that mimics HCV-infected human liver cells and that allows to model patients liver stroma-derived HCC risk signature within a timeframe of days.

Figure 3:
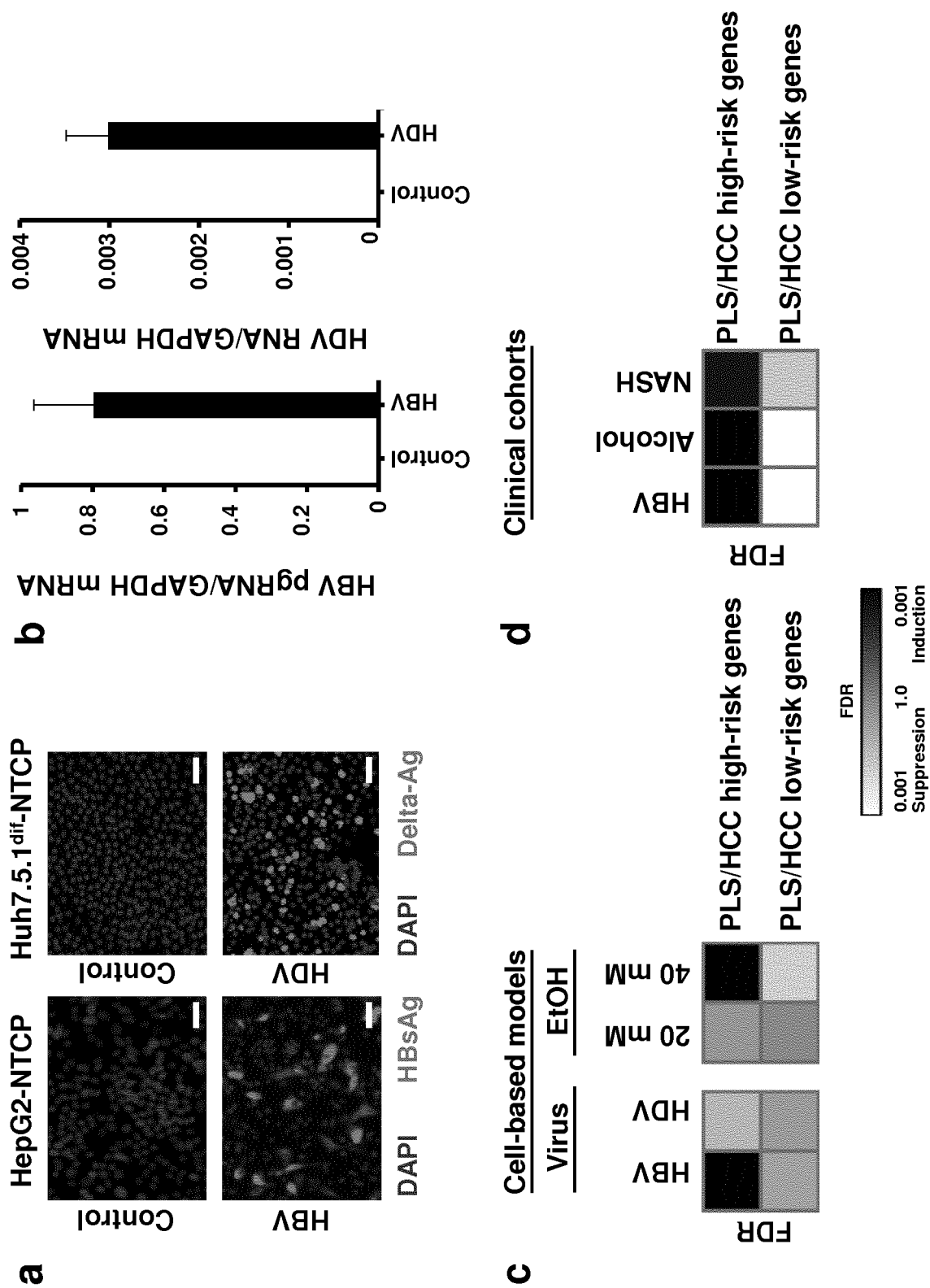
FIG. 3. HBV infection and ethanol exposure induces Prognostic Liver Signature (PLS) in the liver cell-based system similar to clinical cohorts. Liver cells were infected with HBV, HDV or incubated with ethanol. a. Immunodetection of viral antigens in HBV-infected HepG2-NTCP or HDV-infected Huh7.5.1-NTCP$^{dif}$ cells using antigen-specific antibodies. Nuclei were counterstained with DAPI. Scale bar, 50 µm. Results are representative of one out of three experiments. b. Relative HBV pregenomic (pg) RNA and HDV RNA expression in cell-based models as assessed by qRT-PCR (mean±s.d.; n=3). c. 186-gene PLS in cells shown in a as well as in Huh7.5.1$^{dif}$ cells incubated with ethanol. For each condition, the results shown are representative of one experiment performed in triplicate. d. PLS in clinical liver tissues from HBV-related liver disease and HCC (HBV), alcoholic hepatitis (Alcohol) and NASH cohorts. In c and d, heatmaps show the significance of PLS high-/low-risk gene signature induction (black) or suppression (white). FDR: false discovery rate.
Figure 4:
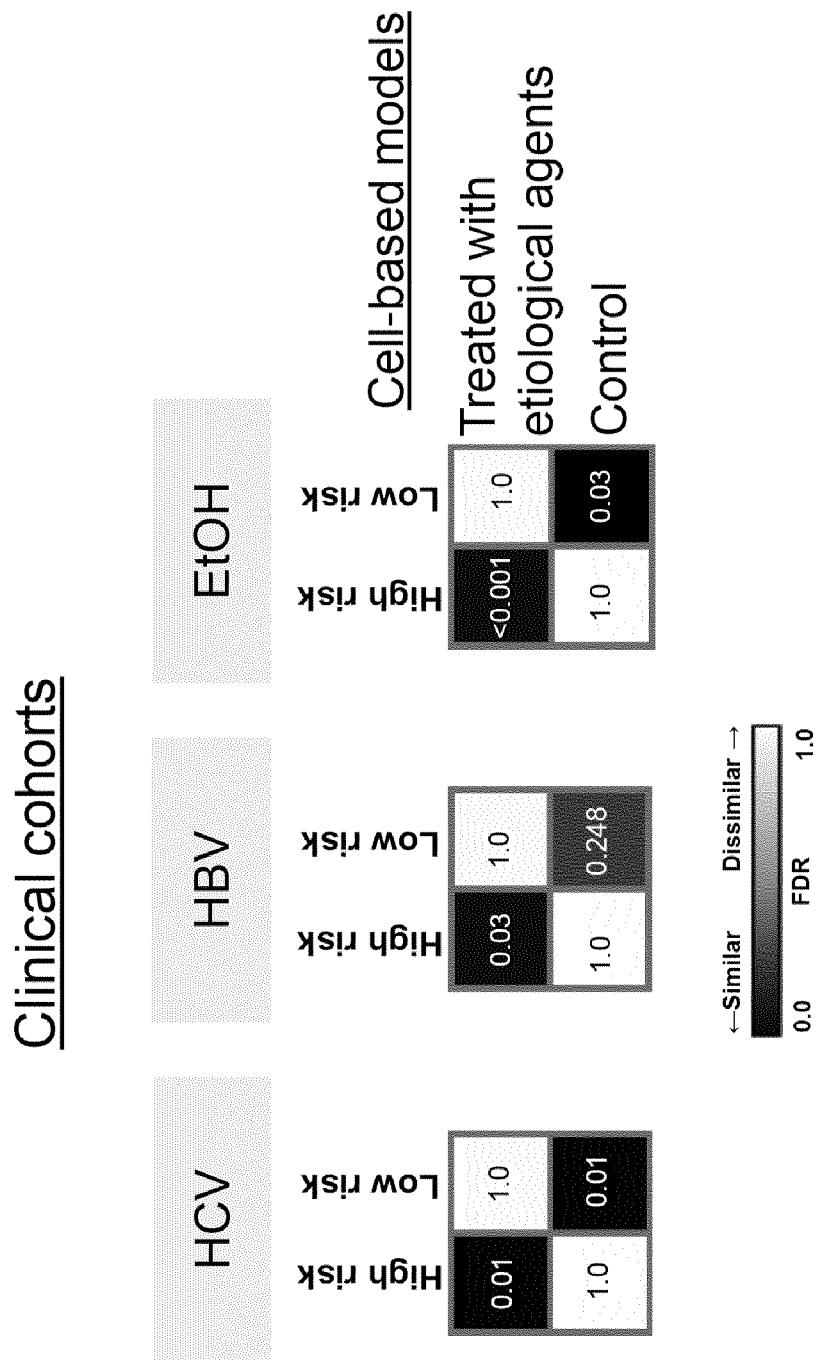
FIG. 4. Similarity of global transcriptome between clinical cohorts and the cell-based models for each major HCC/cirrhosis etiology. Similarities of transcriptome patterns in the cell-based systems (HCV- or HBV-infected, or ethanol-treated, n=3) were compared to liver transcriptome profiles from published clinical cohorts of HCV-related cirrhosis (n=145, NCBI, Gene Expression Omnibus, accession number GSE54100), HBV-related HCC (n=199, GSE14520), and alcoholic hepatitis (n=22, GSE28619) using a bi-directional gene signature-based similarity determination method, Subclass Mapping. Statistically significant similarity was observed between the cells treated with the etiological agents and a subset of patients with poorer prognosis or more severe disease manifestation (FDR<0.25). The resemblance of the PLS low-risk signature genes in the cell-based system with healthier clinical liver was less pronounced in the HBV infection model using HepG2-NTCP cells, currently the only available cell line allowing robust HBV infection. This is consistent with the less differentiated phenotype and morphology of HepG2 cells, which were originally derived from hepatoblastoma, not HCC.

HBV Infection and Ethanol Exposure Induce the HCC Risk Signature in the Liver Cell-Based System Similar to Clinical Cohorts. The Applicants investigated whether the gene signature was also induced in liver cell-based models by other hepatocarcinogenic agents, including HBV and alcohol. To address this question, they used liver cell lines over-expressing NTCP, a recently identified cell entry factor that confers susceptibility to HBV (HepG2-NTCP cells) (Verrier et al., Hepatology, 2016, 63: 35-48) and hepatitis D virus (HDV) infection (Ni et al., Gastroenterology, 2014, 146: 1070-1083), as well as Huh7.5.1$^{dif}$ cells chronically exposed to ethanol. They observed that persistent HBV infection (see FIG. 2a-b) and chronic ethanol incubation at higher dose each resulted in a similar induction of the HCC high-risk genes in cell culture models (FIG. 3c). In contrast, HDV, another hepatotropic virus that requires co-infection with HBV for persistent infection and disease manifestation, did not induce the HCC risk signature by itself (see FIG. 2a-c). Most importantly, induction of the HCC high-risk genes mirrored closely the transcriptional reprogramming in patients with progressive liver disease caused by HBV and alcohol based on the analysis of previously published genome-wide transcriptome profiles. The gene signature observed in cell-based models was similarly induced in diseased human liver in association with poorer prognosis of HCV-related cirrhosis as shown in Applicant's recent study (King et al., Gut, 2015, 64: 1296-1302) and HBV-related HCC (Roessler et al., Cancer Res., 2010, 70: 10202-10212), presence of alcoholic hepatitis (Affo et al., Gut, 2013, 62: 452-460), and more fibrotic NASH (Moylan et al., Hepatology, 2014, 59: 471-482), as shown in FIG. 2d. Direct comparison of the global transcriptome between the cell-based systems and the clinical cohorts also showed significant similarity within each etiology (FIG. 4). However, the resemblance of the HCC low-risk signature genes in the cell-based system with healthier clinical liver was less pronounced in the HBV infection model using HepG2-NTCP cells, which is currently the only available cell line allowing robust HBV infection (FIG. 4, FIG. 2a-b). This is consistent with the less differentiated phenotype and morphology of HepG2 cells, which were originally derived from hepatoblastoma, not HCC (Lopez-Terrada et al., Hum. Pathol., 2009, 40: 1512-1515).

Taken together, the results obtained suggest that the present liver cell-based system reflects transcriptional reprogramming common to the etiological agents capable of promoting HCC development, thereby offering unique opportunities to interrogate the mechanisms of hepatocarcinogenesis and to test cancer preventive strategies for each of the major HCC etiologies.

Co-culture with Non-Parenchymal Liver-Resident Pericytes Models the Liver Microenvironement for the Induction of HCC Risk Signature. The liver microenvironment has been suggested to play an important role in liver disease progression and HCC development (Zhang et al., Hepatology, 2012, 56: 769-775). The hepatic stellate cell is a non-parenchymal liver-resident pericyte well known for driving liver fibrogenesis and supporting carcinogenesis (Zhang et al., Hepatology, 2012, 56: 769-775). The Applicants have previously observed evidence of a hepatic stellate cell activation trait encoded in the HCC risk signature (Hoshida et al., Gastroenterology, 2013, 144: 1024-1030). To investigate the impact of the non-hepatocyte fraction, particularly hepatic stellate cells, on the biogenesis of the signature, the Applicants performed co-culture of Huh7.5.1$^{dif}$ cells with immortalized hepatic LX-2 stellate cells (Xu et al., Gut, 2005, 54: 142-151). Co-culture with stellate cells was found to further enhance induction of the gene signature in a cell- and dose-dependent manner (FIG. 1d). These findings suggest that hepatocytes alone are sufficient for generating the HCC high-risk gene signature, but this can be amplified through cross-talk with non-parenchymal cells. Furthermore, the co-culture system enables to study hepatocyte-hepatic stellate cell interactions that produce a cancer-permissive cirrhotic tissue microenvironment.

Identification of Candidate Drivers of HCC High-Risk Genes Common to Viral and Metabolic HCC Etiologies. To first gain insight into the cell circuits driving the HCC risk signature, the Applicants performed a time-course transcriptomic profiling of HCV-infected hepatocyte-like Huh7.5.1$^{dif}$ cells. Genome-wide profiling of the cells at later time points after HCV infection revealed gradual modulation of pathways involved in a carcinogenesis-supporting tissue microenvironment analogous to that seen in clinical cohorts of virus-infected patients (Hoshida et al., J. Hepatol., 2014, 61: S79-90). Persistent HCV infection in hepatocyte-like Huh7.5.1$^{dif}$ cells was found to induce immune response-related pathways, growth factor signaling pathways, and enhanced cell cycle, DNA replication, and anti-apoptotic pathways. Interestingly, persistent viral infection suppressed a range of metabolic pathways involved in physiological functions of hepatocytes, including cytochrome P450-based xenobiotic metabolism, amino acid biosynthesis, fatty acid and lipid metabolism, and steroid biosynthesis. The impact of HCV infection on the cellular metabolic circuitry was examined directly by using mass spectrometry-based metabolomic profiling (Nicolay et al., Genes Dev., 2013, 27: 182-196).

Analysis of the metabolic phenotype revealed alterations in steady-state metabolites in virus-infected cells, including pronounced increases in lactate and glutamine levels in parallel to elevated influx of glucose and intracellular glucose consumption (data not shown)—a Warburg-like metabolic shift associated with increased cancer risk (Cantor et al., Cancer Discov., 2012, 2: 881-898; Chen et al., Free Radic. Biol. Med., 2015, 79C: 253-263). This is also consistent with the enrichment of a carbohydrate metabolism gene expression signature, which was the only metabolic pathway significantly activated by HCV infection.

Figure 5:
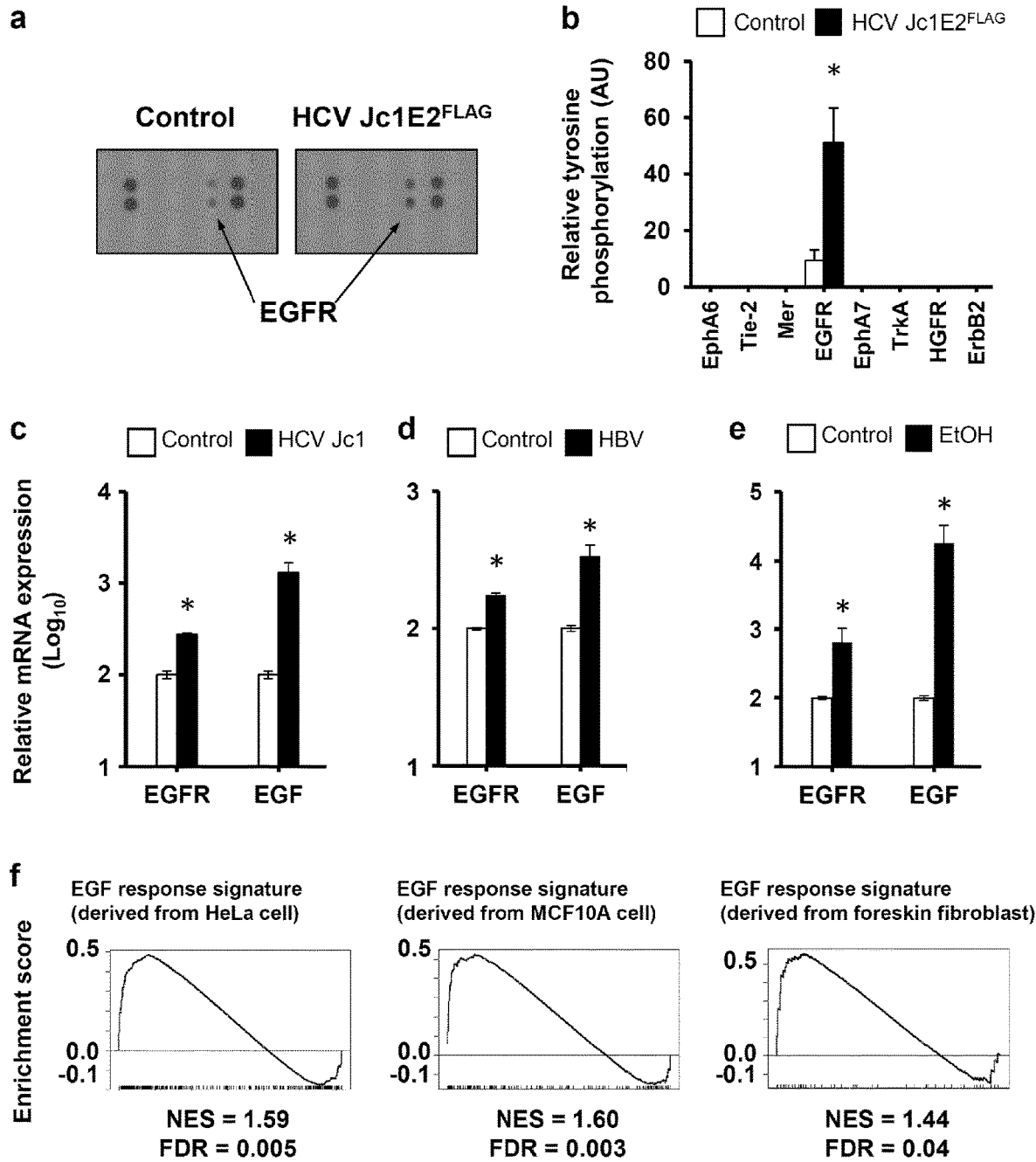
FIG. 5. EGFR signaling is a pan-etiology driver of the Prognositc Liver Signature (PLS) high-risk genes in human liver cells. Huh7.5.1$^{dif}$ cells were infected with HCV Jc1E2$^{FLAG}$ and harvested for proteomic analyses as shown in FIG. 1. a. Receptor tyrosine kinase (RTK) phosphorylation was assessed in cell lysates using the Human Phospho-RTK Array Kit. Infection with HCV Jc1E2$^{FLAG}$ results in increased EGFR phosphorylation. One representative experiment out of three is shown. b. Quantification of dot blot intensities of phosphorylated proteins (in arbitrary units, AU) using the Image J software. The results show the mean±SEM of integrated dot blot densities from three independent experiments performed in duplicate. c-e. EGFR and EGF mRNA expression (relative to GAPDH mRNA) in non-infected (Control) and HCV Jc1-infected Huh7.5.1$^{dif}$ cells (c; n=9); non-infected (Control) and HBV-infected HepG2-NTCP cells (d; n=9); Huh7.5.1$^{dif}$ cells incubated in absence (Control) or presence of 40 mM ethanol (e; n=12). Mean percentage of control±SEM (log 10 scale) is shown. f. Virus-mediated signaling induces an EGF signature in HCV Jc1-infected Huh7.5.1$^{dif}$ cells. The panels show the presence of previously reported EGF-related gene signatures derived from other cell lines assessed by GSEA in virus-infected Huh7.5.1$^{dif}$ cells. FDR: false discovery rate; NES: normalized enrichment score. *Two-tailed Mann-Whitney U-test (p-value<0.01) in b-e.

The gene signature induced by HCV infection or HBV infection, or by ethanol treatment reflects modulation of carcinogenic pathways common to the etiological agents capable of promoting HCC development. Nine out of 73 HCC high-risk genes most prominently induced across HCV, HBV, and ethanol in the present cell-based models (whose deregulation was independently validated by qRT-PCR analyses as shown in FIG. 5d-e) represented oxidative stress response (e.g. glutathione peroxidase 2, GPX2), extracellular matrix remodeling (e.g., lysyl oxidase-like 2, LOXL2), and growth factor signaling (e.g., epidermal growth factor, EGF; dual specificity protein phosphatase 5, DUSP5) (see Table 2). Accordingly, there was strong enrichment of cancer-related pathways (see Table 3) and two co-regulated gene networks involved in inflammation/fibrogenesis (containing EGF) and oxidative stress/carcinogenesis (containing p53/Myc).

TABLE 2

PLS/HCC high-risk signature genes commonly induced by HCV, HBV and ethanol in liver cell-based systems. Genes contributing to the GSEA enrichment (core enrichment genes) that are common to HCV/HBV infection and alcohol treatment are shown.

| Gene Symbol | Gene title | Entrez Gene ID |
|---|---|---|
| ANXA1 | annexin A1 | 301 |
| ANXA3 | annexin A3 | 306 |
| DUSP5 | dual specificity phosphatase 5 | 1847 |
| EGF | epidermal growth factor | 1950 |
| FILIP1L | filamin A interacting protein 1-like | 11259 |
| GPX2 | glutathione peroxidase 2 (gastrointestinal) | 2877 |
| LOXL2 | lysyl oxidase-like 2 | 4017 |
| PODXL | podocalyxin-like | 5420 |
| SLC12A2 | solute carrier family 12 (sodium/potassium/chloride transporter), member 2 | 6558 |

TABLE 3

Enriched canonical pathways in HCC high-risk genes common to HCV, HBV and ethanol-treated liver cell-based models (Ingenuity Pathway Analysis). Pathways with enrichment p-value less than 0.05 are shown.

| Pathway | p-value |
|---|---|
| Glutathione Redox Reactions I | 0.008 |
| EGF Signaling | 0.025 |
| Regulation of Cellular Mechanics by Calpain Protease | 0.025 |
| ERK5 Signaling | 0.028 |
| Non-Small Cell Lung Cancer Signaling | 0.029 |
| Macropinocytosis Signaling | 0.030 |
| Caveolar-mediated Endocytosis Signaling | 0.032 |
| HER-2 Signaling in Breast Cancer | 0.034 |
| ErbB Signaling | 0.038 |
| Bladder Cancer Signaling | 0.038 |
| FAK Signaling | 0.038 |
| Neurogulin Signaling | 0.039 |
| Glioma Signaling | 0.042 |
| Telomerase Signaling | 0.044 |
| Pancreatic Adenocarcinoma Signaling | 0.047 |

EGFR Signalling is a Pan-Etiology Driver of the HCC High-Risk Signature in Human Liver Cells. The Applicants have previously shown that HCV uses receptor tyrosine kinases including EGFR and activation of downstream signaling pathways to enter hepatocytes in cell culture and in vivo (Lupberger et al., Nature Med., 2011, 17: 589-595; Zona et al., Cell Host Microbe, 2013, 13: 302-313). To assess whether HCV exploits receptor tyrosine kinases not only for entry, but also to trigger intracellular signaling cascades relevant to the induction of the HCC risk signature, they investigated virus-induced signaling in infected liver cells. Using the cell-based model system described herein, they screened the activation state of canonical signaling pathways using phospho-receptor tyrosine kinase arrays and gene expression analyses. They observed that HCV infection triggers activation of specific host signaling networks, including the EGFR pathway as shown by virus-induced EGFR phosphorylation (FIG. 5a-b), enhanced EGF and EGFR expression and significant induction of experimentally defined EGF target gene signatures (Amit et al., Nature Genet., 2007, 39: 503-512; Zhang et al., Angiogenesis, 1999, 3: 211-219) (FIGS. 5c and f). Interestingly, induction of the EGF/EGFR pathway was also observed in HBV-infected cells, and in ethanol-treated cells (FIG. 5d-e), confirming EGF as a driver of the HCC risk signature common to the major HCC etiologies. Pharmacological inhibition of the EGF/EGFR pathway with erlotinib at concentrations that did not modify HCV viral load suppressed the HCC high-risk genes as observed in Applicants previous in vivo HCC chemoprevention study (Fuchs et al., Hepatology, 2014, 59: 1577-1590) (FIG. 5a, c-d). Transcriptome-based network analysis indicated that this drug impacts on a fibrosis network involving the EGFR/MAPK signaling pathway and a p53/Myc-related carcinogenesis network (FIG. 5e-f). The functional impact of the EGFR/MAPK signaling pathway was corroborated by perturbation studies using the Ras inhibitor tipifarnib and the ERK1/2 inhibitor Fr180204 (FIG. 5a-d). Inhibition of virus-induced MAPK signaling as shown by reduced ERK1/2 phosphorylation (FIG. 5b) at low inhibitor concentrations with absent effects on viral load (FIG. 5c) suppressed the HCC high-risk gene signature in differentiated liver cells (FIG. 5d). Thus, it is likely that the pharmacological inhibitors reverse the gene signature through direct suppression of EGF-induced oncogenic pathways independently of any antiviral effect. Collectively, these data demonstrate that the model system combined with perturbation studies enables to investigate drivers of the cell circuits associated with liver disease progression and hepatocarcinogenesis.

The Applicants next assessed the utility of the gene signature as a companion biomarker in the HCC chemoprevention trial of erlotinib. To this end, they used erlotinib to treat organotypic ex vivo cultures of surgically resected human fibrotic liver tissue slices from two HBV-infected HCC patients. Notably, erlotinib was found to effectively suppress the HCC high-risk genes in these human tissues (data not shown). Collectively, the data presented here show that EGFR/Ras/MAPK signaling is an etiology-independent driver of the HCC high-risk signature in the human liver. Furthermore, these results indicate that the effect of pharmacological interventions on the carcinogenic milieu-related cellular circuits can be evaluated in a tractable cell-based system.

Cell-based screen of computationally-enriched small molecules identifies candidate compounds for prevention and treatment of liver cirrhosis/HCC and HCC/cirrhosis chemoprevention. Molecular signature-based in silico drug screening has been shown to be an effective way to identify or repurpose existing drugs for new indications, and enrich compounds to be experimentally screen to improve success rate in a cost-effective manner. Association of the molecular signature with clinical prognosis, not mere experimental phenotypes, will considerably strengthen clinical relevance of the prioritized compounds. However, such cellular models are not easily available for specific diseases. The results obtained in the present study clearly indicate that the liver cell model systems serve as a platform for drug discovery for prevention and treatment of cirrhosis and HCC/cirrhosis chemoprevention. To test this hypothesis, the Applicants first informatically interrogated two chemogenomics databases to select compounds likely to reverse the HCC risk signature in silico (see Materials and Methods above). It is shown below that the present systems enables identification of candidate drivers of the HCC risk signature and to uncover compounds for prevention and treatment of liver cirrhosis and HCC/liver cirrhosis chemoprevention.

Figure 6:
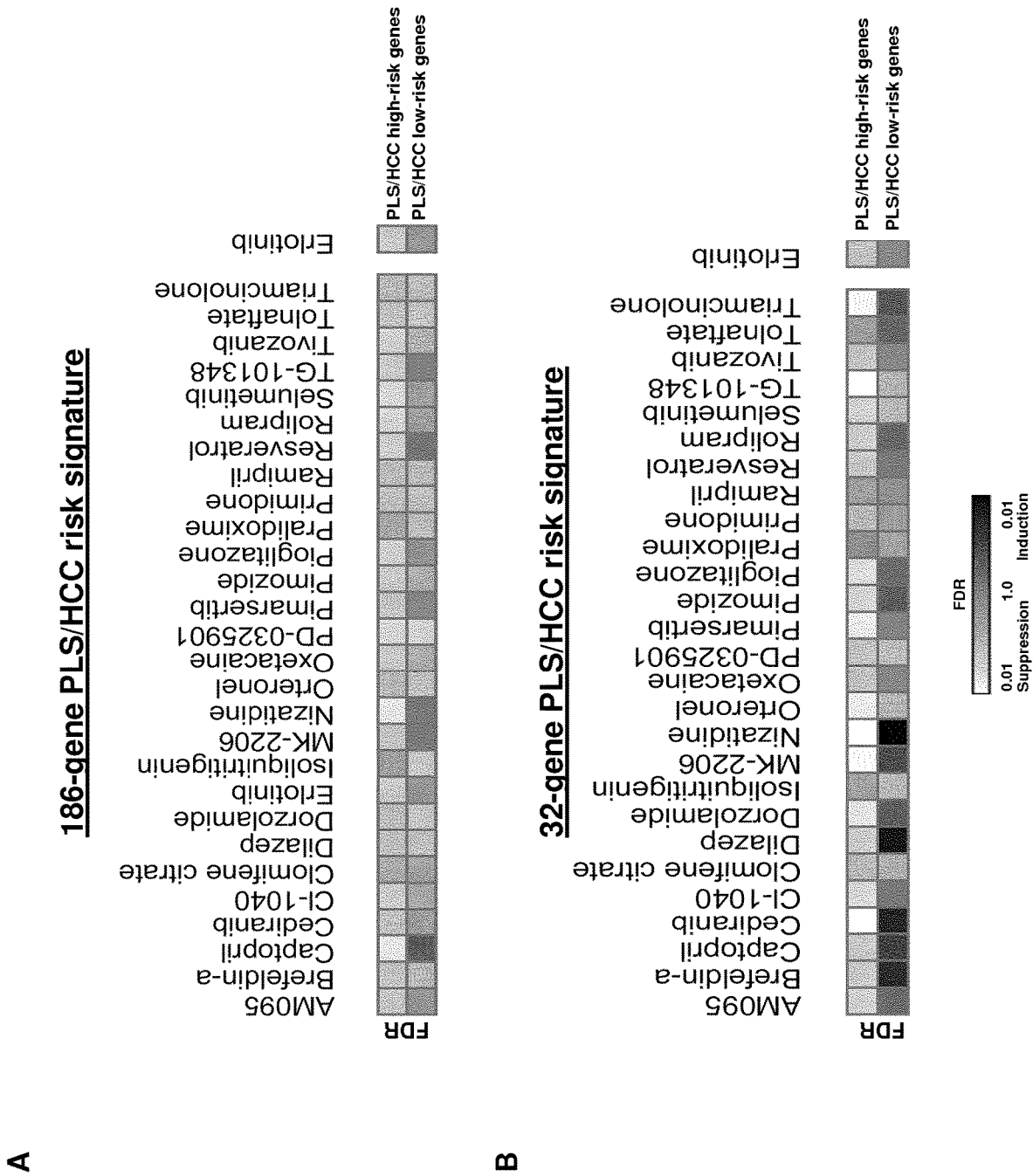
FIG. 6. Perturbation studies based on chemogenomics identify candidate compounds for HCC chemoprevention. Twenty-nine prioritized compounds were evaluated for HCC chemoprevention in HCV-infected Huh7.5.1$^{dif}$ cells by using the NCOUNTER assay in a screen format. Huh7.5.1$^{dif}$ cells were seeded in P96-well format and maintained in 1% DMSO-completed medium. Cells were infected with HCV. Seven days after infection, cells were incubated with the different drugs. After three days of treatment, cell lysates were subjected to NCOUNTER Digital Analyzer system (NanoString). The heatmaps show the significance of induction (black) or suppression (white) of high- and low-risk genes of the PLC/HSS a.186- or b. 32-gene signature in drug-treated liver cells versus non-treated cells. Results are from three independent experiments.
Figure 11:
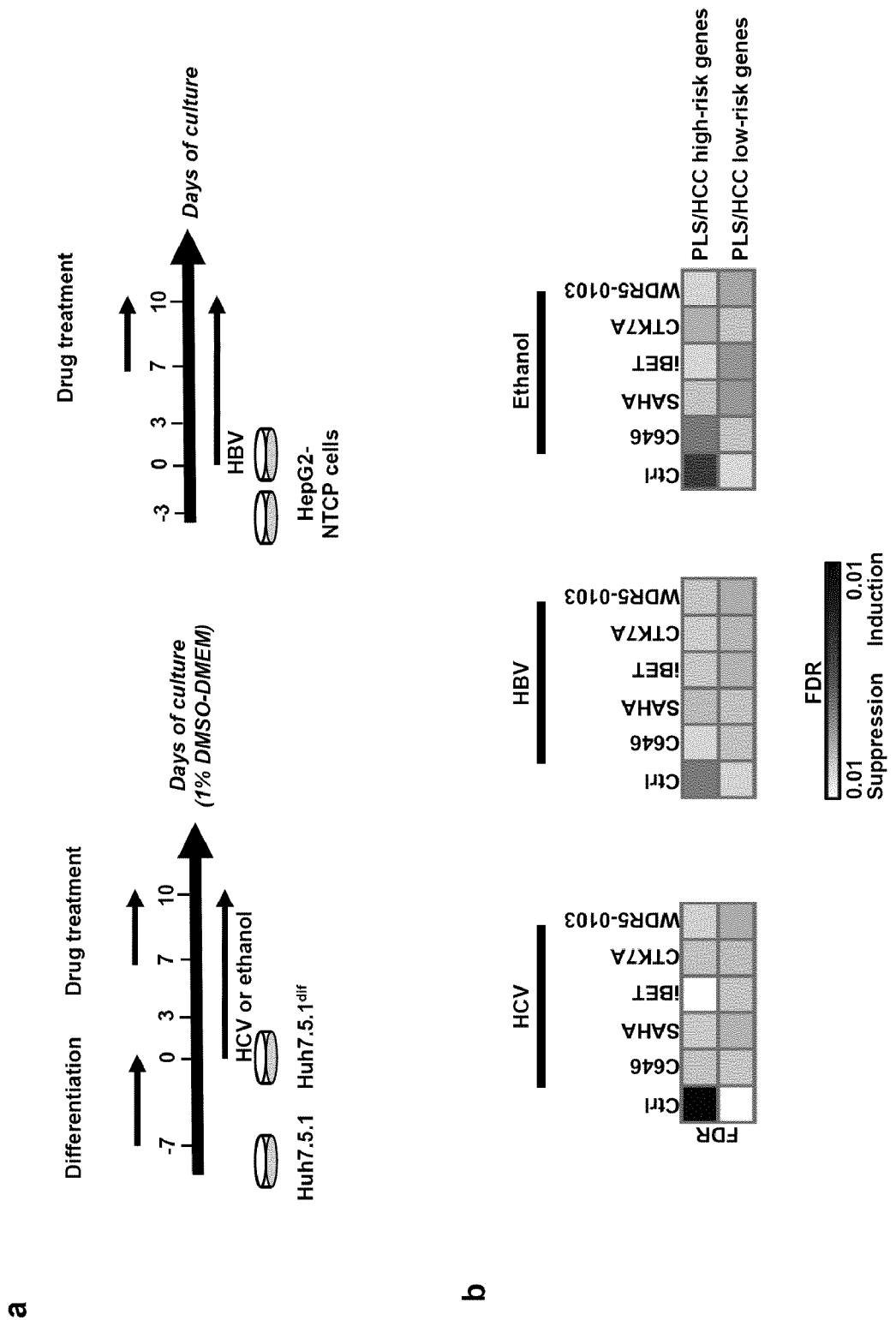
FIG. 11. A patient-derived pan-etiology 32-gene PLS/HCC risk signature is reversed by epigenetic inhibitors targeting chromatin remodeling as candidate compounds for HCC chemoprevention. a. Approach: Huh7.5.1$^{dif}$ cells were seeded in P6-well format and maintained in 1% DMSO-complemented medium. Cells were infected with HCV or exposed to ethanol (40 mM). HepG2-NTCP cells were seeded in P12-well format and were infected with HBV. Nine or seven days after infection, cells were incubated with the different epigenic inhibitors. Total RNA was isolated and subjected to NCOUNTER Digital Analyzer system (NanoString) or high-throughput qRT-PCR Biomark HD. b. Heatmap showing the significance of PLS/HCC high-/low-risk gene induction/suppression following treatment with different inhibitors. In scale bar, grey indicates significant suppression, black indicates significant induction. FDR values that are less than 0.25 were considered significant. FDR: false discovery rate. Results are from three independent experiments.

Among the prioritized compounds, the Applicants identified 24 small molecules that significantly and markedly suppressed the HCC risk signature (FIGS. 6 and 11, Table 4—see also Example 5) without detectable toxicity in the cell system (data not shown). Notably, the effect of these compounds on the HCC risk gene expression was not due to a decrease in viral load (data not shown). Interestingly, several of the identified compounds (Captopril, Cl-1040, Dilzep, Dorzolamide, Nizatidine, Orteronel, Pimarsetinib, Rolipram, TG-101348, iBET, C646 and WDR5-0103 have never been indicated for HCC chemoprevention or treatment. Collectively, these data demonstrate that the cell system enables to discover non-liver toxic drugs for HCC chemoprevention in a robust and simple format.

Taking advantage of the tractable model mimicking a cancer-permissive cirrhotic tissue microenvironment, the Applicants identified bioactive compounds capable of threatening cirrhosis and reducing HCC risk in cirrhotic liver and suitable for long-term administration in patients with diseased liver.

Figure 7:
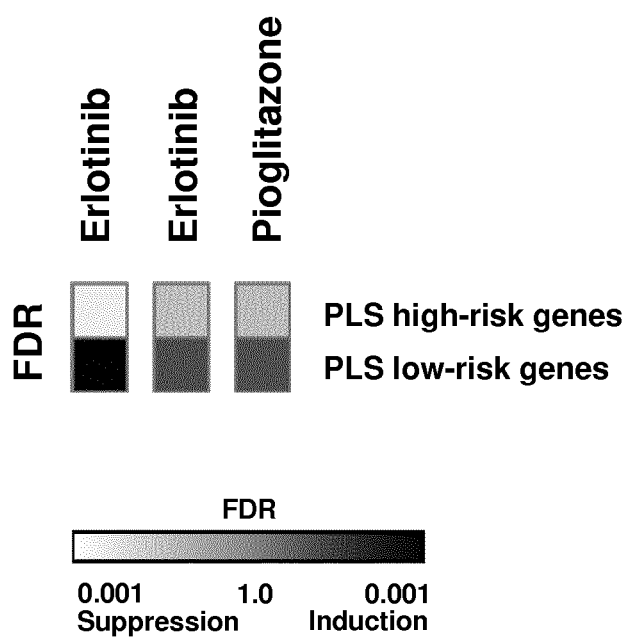
FIG. 7. Ex vivo validation. Liver tissue sections from surgically resected fibrotic livers (patients #1 and #2: HBV-infected liver tissue; patient #3: NASH liver tissue) express the Prognositc Liver Signature (PLS), which is reverted by treatment with erlotinib (5 µM for 48 hours) or pioglitazone (10 µM for 10 hours). Modulation of the HCC high-risk genes in treated liver tissues was quantitatively assessed by GSEA as in FIG. 6.

Ex vivo Validation of Candidate Drugs in Human Liver Tissues. Next, the Applicants validated the functional impact of two screen-derived compounds by ex vivo experiments: pioglitazone, which is currently in clinical use for the treatment of type 2 diabetes and NASH, and captopril a well-established anti-hypertensive drug. They confirmed and validated the functional effect of pioglitazone on the HCC risk signature in organotypic ex vivo culture of fibrotic human liver tissue (FDR=0.046, FIG. 7a). Overall, this validation of data in human liver tissue supports the validity of the system to efficiently bridge preclinical to clinical evaluation of novel HCC chemoprevention agents, ensuring relevance by relying on the clinically well-validated HCC risk signature.

Taken together the present results suggest that the cell-based screening system can be used to further refine hits from the in silico analysis to identify the best compounds to be examined in more time-consuming and costly animal experiments. The combination of in silico and cell-based screening with subsequent in vivo and ex vivo validation paves the way for fast-track HCC chemopreventive drug discovery.

Discussion

There is an unmet need for experimental systems modelling human disease-specific gene expression to understand disease biology and enable disease-specific drug discovery. In the present study, the Applicants have developed a simple and robust liver cell-based system that closely recapitulates the transcriptional reprogramming in patients with carcinogenic liver disease caused by HCV, HBV and alcohol. Notably, the workflow presented here permits robust and rapid modeling of gene expression patterns predictive of long-term HCC risk in patients with decades of chronic disease. This cell-based system further enables modeling of inter-cell type cross-talk in a cancer-permissive cirrhotic tissue microenvironment as shown by co-culture of hepatocytes and hepatic stellate cells, liver-resident pericytes that drive fibrogenesis (FIG. 1d). Overall, the disclosed cell model offers unique opportunities to investigate the molecular mechanisms and cell circuits that drive hepatocarcinogenesis across the distinct HCC etiologies. Indeed, using this system, the Applicants have uncovered the functional role of EGFR as a pan-etiology driver of the HCC high-risk signature. Perturbation studies using small molecule inhibitors confirmed the functional impact of EGFR/MAPK signaling for the biogenesis of the HCC risk signature. Furthermore, computational analyses revealed previously undiscovered candidate drivers of this gene signature and hepatocarcinogenesis. These include oxidative stress response (e.g. GPX2), extracellular matrix remodeling (e.g. LOXL2), and growth factor signaling (e.g. EGF, DUSP5), which are now linked to long-term clinical HCC risk via a patient-derived gene signature. Since oxidative stress response-related genes such as KEAP1 and NFE2L2 are frequently inactivated by somatic DNA mutations in HCC (Totoki et al., Nature Genet., 2014, 46: 1267-1273), GPX2 may be a useful marker to monitor the pathway and/or serve as a point of intervention by antioxidants to rescue this pathway. Monoclonal antibody (simtuzumab) and small molecule inhibitors targeting LOXL2 protein are currently under clinical evaluation as anti-liver fibrosis agents and very recent studies suggest also a role of LOXL2 for hepatocarcinogenesis, which may be prevented by simtuzumab (Wong et al., Hepatology, 2014, 60: 1645-1658). Assessment of the HCC risk signature in these trials may provide insight into the potential role of these drugs in HCC prevention. EGFR, MAPK and DUSP5 are closely linked within the same pathway as phosphatase DUSP5, whose expression is induced by MAPK signaling, regulates the nuclear phosphorylation of ERK. Importantly, similar pathways and networks were present in liver tissues from HBV-related or alcoholic liver disease and NASH, supporting the clinical relevance of the findings.

Thus, the present results uncover EGF, GPX2, and LOXL2 as targetable candidate drivers for liver disease and HCC progression common to viral and metabolic etiologies associated with chronic inflammation, fibrogenesis, and hepatocyte turnover/proliferation that collectively incite a cancer-permissive milieu. Moreover, the results obtained in the present study suggest that the HCC risk signature can be used as a companion biomarker universally applicable to HCC chemoprevention therapies targeting these pathways. Collectively, these findings highlight the impact of the Applicants' cell-based system for the discovery of clinically relevant targets of hepatocarcinogenesis.

One reason for the absence of HCC chemopreventive strategies has been the lack of robust and convenient experimental systems to model and investigate clinically-relevant mechanisms and targets in HCC development. Moreover, current animal models for HCC only partially recapitulate human disease and preclude fast-track drug discovery and development. The opportunity to perform perturbation studies using small molecules in the present clinical signature-inducible cell-based system not only allows the discovery of the cell circuits of hepatocarcinogenesis, but also paves the way for systematic and high-throughput drug screening to discover novel therapeutic strategies that block the progression of fibrosis/cirrhosis to HCC.

Taking advantage of the present tractable cell model system, the Applicants unraveled 24 bioactive compounds suitable for long term administration in patients with liver disease that are capable of reducing HCC risk in cirrhotic liver (see Table 4).

Mechanistically, it is likely that EGFR and MAPK signaling contributes to the preventive activity of the drugs. Indeed, by exploring the LINCS database (website: lincscloud.org), the Applicants discovered that pioglitazone modulates EGF and MAPK signaling, which is a hallmark and driver of the HCC risk signature. Transcriptome-based network analyses revealed that pioglitazone perturbed the two gene networks, i.e., EGF-containing fibrogenesis network and p53/Myc-containing carcinogenesis network common to erlotinib. Interestingly, captopril has also been suggested to impair EGFR signaling (Oikawa et al., Life Sci., 2014, 97: 137-144). Since the present data show that EGFR:MAPK signaling is a key driver of the HCC risk signature, it is likely that this pathway plays a mechanistic role for HCC prevention for the identified compounds.

In conclusion, the ability to efficiently identify, from computationally-enriched compounds, candidate HCC chemoprotective agents using the cell-based system described herein will greatly expedite the progress of HCC chemoprevention drug development and substantially improve the dismal prognosis of patients with cirrhosis at risk of HCC.

Example 2: Liver Nonparenchymal Co-culture Systems Model for Biomarker and Drug Discovery to Prevent and Treat Liver Disease Progression and Liver Cancer Development The Applicants performed co-culture studies of hepatocyte-like cells with either stellate cell lines or Kupffer cells, and studied the impact of non-parenchymal cells on the transcriptional reprogramming, which is associated with the genesis of the HCC risk signature.

Materials and Methods

Cell lines and culture. Hepatocellular carcinoma-derived Huh7.5.1 (Zhong et al., PNAS USA, 2005, 102: 9294-9299) and human stellate LX-2 or TWNT-4 cells (Xu et al., Gut, 2005, 54: 142-151; Shibata et al., Cell Transplant., 2003, 12: 499-507) have been described. Human THP-1 monocytes and Kupffer cells were obtained from ATCC and Life Technologies, respectively. For co-culture experiments, $2.5 \times 10^4$ Huh7.5.1 cells were seeded together with 10% of total cells of either LX-2 or TWNT-4 hepatic stellate cells or 20% of THP-1 cells. Furthermore, $5 \times 10^3$ Huh7.5.1 cells were seeded with $7 \times 10^4$ non-proliferating Kupffer cells in order to have approximately 20%-50% of Kupffer cells at the end of the co-culture. All co-cultures were maintained for 17 days in 1% DMSO-complemented medium.

HCV infection. Co-cultures were infected with recombinant HCV Jc1 (Majzoub et al., Cell, 2014, 159: 1086-1095) (genotype 2a/2a; $TCID_{50}/mL=\sim1\times10^6/mL$) or incubated with supernatants from mock-electroporated cells. HCV infection was assessed by qRT-PCR of intracellular HCV RNA (Xiao et al., PLoS Pathog., 2014, 10: e1004128).

Transcriptional analyses. Ten days after HCV Jc1 infection, co-cultures were lysed using TRI-reagent (MRC) and RNA purified using the Directzol mini kit (Zymo Research). Gene expression profiling was performed using 250-500 ng total RNA by using either NCOUNTER Digital Analyzer system (NanoString). Induction or suppression of PLS was determined by Gene Set Enrichment Analysis (GSEA), implemented in GenePattern genomic analysis toolkits (Hoshida, PLoS One, 2010, 5(11): e15543; Subramanian et al., PNAS USA, 2005, 102: 15545-15550; Reich et al., Nature Genet., 2006, 38:500-501).

Results and Conclusions

Figure 8:
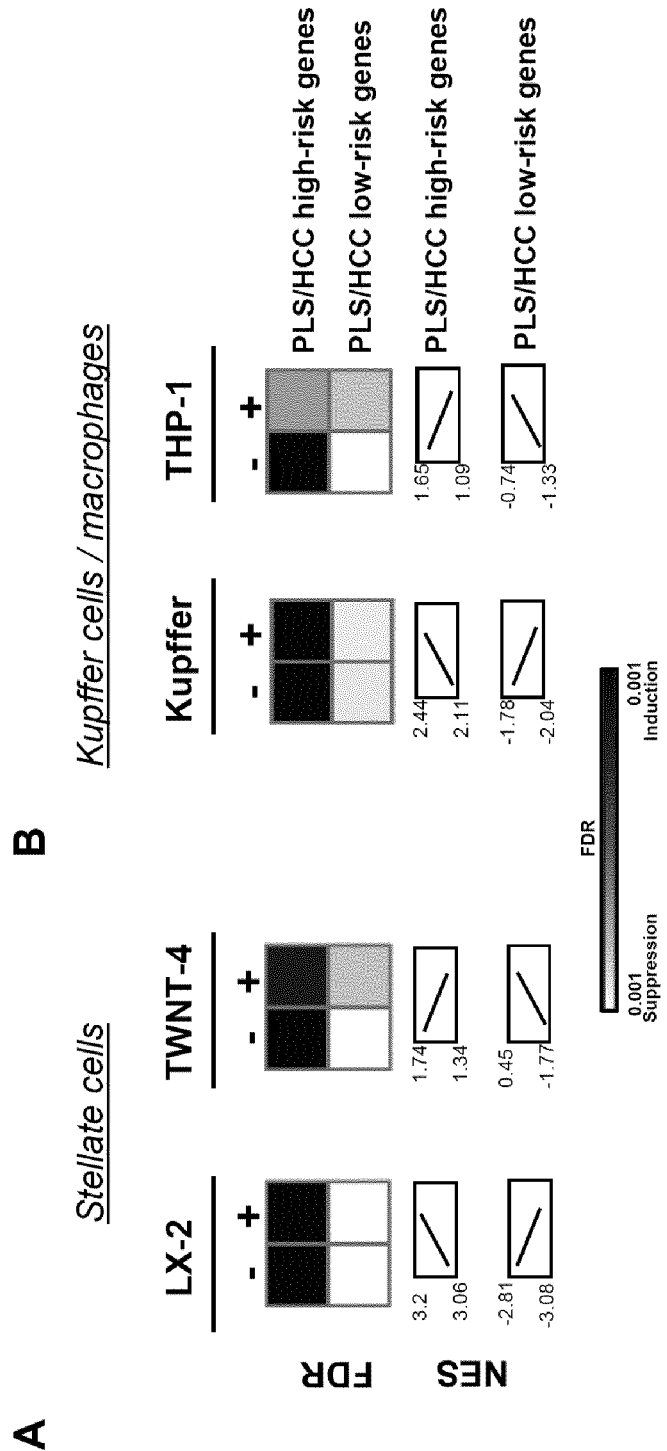
FIG. 8. Co-culture with non-parenchymal liver cells models the liver microenvironment for the induction of the 186-gene PLS risk signature. Huh7.5.1$^{dif}$ cells were co-cultured with stellate cell lines LX-2 and TWNT-4, Kupffer cells or THP1 cells—a monocytic control cell line. Cells were incubated with HCV Jc1 and cultured for 7 days. On day 10 post-infection, RNA was isolated and the 186-gene HCC risk signature was profiled. A. Gene expression profiles in co-culture with hepatic stellate cell lines, LX-2 or TWNT-4. B. Gene expression profiles in co-culture with Kupffer cells or a macrophage/monocyte model cell line, THP1. Heatmaps (top) showing the significance of high-/low-risk gene induction/suppression in cells. Graphs (bottom) shows the modulation of the gene expression normalized enrichment score (NES). In scale bar, white indicates suppression, black indicates induction. FDR values that are less than 0.25 were considered significant. FDR: false discovery rate; NES: normalized enrichment score. (−) mono-culture (+) co-culture.

Co-culture of hepatocyte-like cells with stellate or Kupffer cells models the liver microenvironment for the induction of the HCC risk signature. To investigate the involvement of the non-hepatocyte fraction, particularly hepatic stellate cells (HSC) and macrophages, on the biogenesis of the signature, the Applicants performed co-culture of hepatocyte-like cells with non-parenchymal liver cells. As compared to monoculture of HCV-infected hepatocyte-like cells, co-culture with immortalized hepatic LX-2 stellate cells (Xu et al., Gut, 2005, 54: 142-151) further enhanced induction of the gene signature (FIG. 8A). Likewise, co-culture of Kupffer cells and hepatocyte-like cells resulted in a pronounced modulation of the signature as compared to monoculture of hepatocyte-like cells (FIG. 8B). In contrast, co-culture with TWNT-4 (FIG. 8A), a different human stellate cell line or THP-1 (FIG. 8A), a cell line derived from an acute monocytic leukemia (Tsuchiya et al., Int. J. Cancer, 1980, 26: 171-176), did not exert significant effect on the modulation of the signature at the experimental conditions shown in FIG. 8. To gain insights into the molecular mechanisms driving the enhancement of the HCC high-risk genes in co-cultures, the Applicants characterized the most differentially expressed genes between virus-exposed co-culture and liver cell monoculture through leading-edge analyses. In Huh7.5.1/LX-2 co-cultures, this analysis identified 40 differentially expressed HCC high-risk and 50 low-risk genes, respectively.

The 40 differentially expressed HCC high-risk genes comprise: GPX2, NTS, COL6A3, ANXA1, COL4A1, LOXL2, PSMB9, PODXL, SLC7A1, SP1, ANXA3, TGFB1I1, EGF, IGFBP6, NCAPH, AEBP1, DAB2, GBA, FBN1, CHSY1, TNK2, SLC12A2, CPA3, IER3, ACTR2, IQGAP1, NOL7, RBM34, NFKB2, COL16A1, AP1B1, IFI3, and ABLIM1.

The 50 differentially expressed HCC low-risk genes PLG, GJB1, HMGCR, PPP1R1A, LIPC, SREBF2, C8B, C4BPB, HAAO, CPN1, RLF, CTBS, GCKR, ACOT2, SC5DL, GCGR, CYB5A, PCK1, ADH6, TXN2, RPS6KA5, PON3, AKR1D1, C5, DST, ACSM3, PMM1, ATP5D, TMEM97, ATP2C1, CPOX, ANKRD46, PKLR, BRP44, TM7SF2, F9, PTPN18, IGF1, SUCLG1, SNX1, GSTM1, KCNJ3, HABP2, CALCR, ATP6AP2, IMPA1, PROS1, ALAS1, DLGAP4, and ALDH9A1.

LX-2 stellate and Kupffer cell co-culture models enable to study the functional role of nonparenchymal cells for the induction of the HCC enabling biomarker/drug discovery targeting hepatocyte-nonparenchymal cell interactions. Co-culture with LX-2 stellate cells resulted in significant increase of expression of HCC high-risk genes. Examples include genes involved in the activation of liver myofibroblastic differentiation (SP1), HCC chemoresistance (SLC7A1), tumor angiogenesis and inflammation in liver tumor-initiating cells (NTS), and promotion of HCC epithelial mesenchymal transition (EGF). On the other hand, co-culture with LX-2 stellate cells suppressed genes involved in apoptosis (IGF1) and liver-injury detoxification processes (GSTM1). Kupffer cell co-culture aggravated the expression of HCC high-risk genes. Examples include genes recently shown to be involved in hepatic oxidative stress (GPX2), epigenetic modifications as well as increased liver fat accumulation and disruption of hepatic glucose homoeostasis (HDAC9), formation of tumor microenvironment and metastatic niche (LOXL2), and liver fibrosis (SP100). Furthermore, co-culture with Kupffer cells suppressed genes deleted in HCC (ADH5), mutated in mitochondrial hepato-encephalomyopathy (SUCLG1), and down-regulated during liver fibrosis, leading to fat accumulation (SREBP2).

Co-culture of hepatocyte-like cells with LX-2 stellate or Kupffer cells modified expression of HCC high- and low-risk genes. In conclusion, the liver co-culture model can be used to (1) investigate the role of nonparenchymal cell for pathogenesis of liver disease progression and hepatocarcinogenesis, (2) identify biomarkers for disease progression and cancer related to hepatocyte nonparenchymal cells interaction, and (3) discover and characterize drugs for treatment of liver disease and cancer prevention which target hepatocyte-non parenchymal cell-interactions.

Example 3: Modeling a Patient-Derived Pan-Etiology 32-Gene PLS/HCC Signature in Non-Hepatic Cell Lines to Identify Biomarkers and Drugs Targeting Disease Progression and Cancer in General The Applicants have tested the induction of the 32-gene signature in non-hepatic cancer cell lines derived from the colon (Caco-2/TC7), or the cervix (HeLa) exposed to ethanol, and HCV-permissive human embryonic kidney engineered to express HCV hots factors (293T-4R/miR122) infected with HCV.

Materials and Methods

Cell lines and culture. Hepatocellular carcinoma-derived Huh7 (Verrier et al., Hepatology, 2016: 53: 35-48), and colon Caco-2/TC7 (Mailly et al., Nature Biotechnol., 2015, 33: 549-554) have been described. HeLa cells were obtained from ATCC. Cells were cultured in Dulbecco's Modified Eagle Medium (DMEM). 293T-4R/miR122 cells (described in Da Costa et al., J. Virol., 2012, 86: 11919-11925) were cultured in DMEM containing puromycin and blasticidin.

Ethanol treatment of hepatic and nonhepatic cell lines. Huh7, Huh7.5.1, Caco-2/TC7, and HeLa cells were seeded in 12-well plates and exposed to ethanol (40 mM) for 7-10 days. Fresh medium containing ethanol was replenished daily (Ye et al., Drug and Alcohol Dependence, 2010, 112: 107-116).

HCV infection of permissive hepatic and nonhepatic cell lines. DMSO-diffrentiated Huh7.5.1 and 293T-4R/miR122 cells were infected with recombinant HCV Jc1 (genotype 2a/2a; $TCID_{50}/mL=\sim1\times10^6/mL$) or incubated with supernatants from mock-electroporated cells. HCV infection was assessed by qRT-PCR of intracellular HCV RNA.

Figure 9:
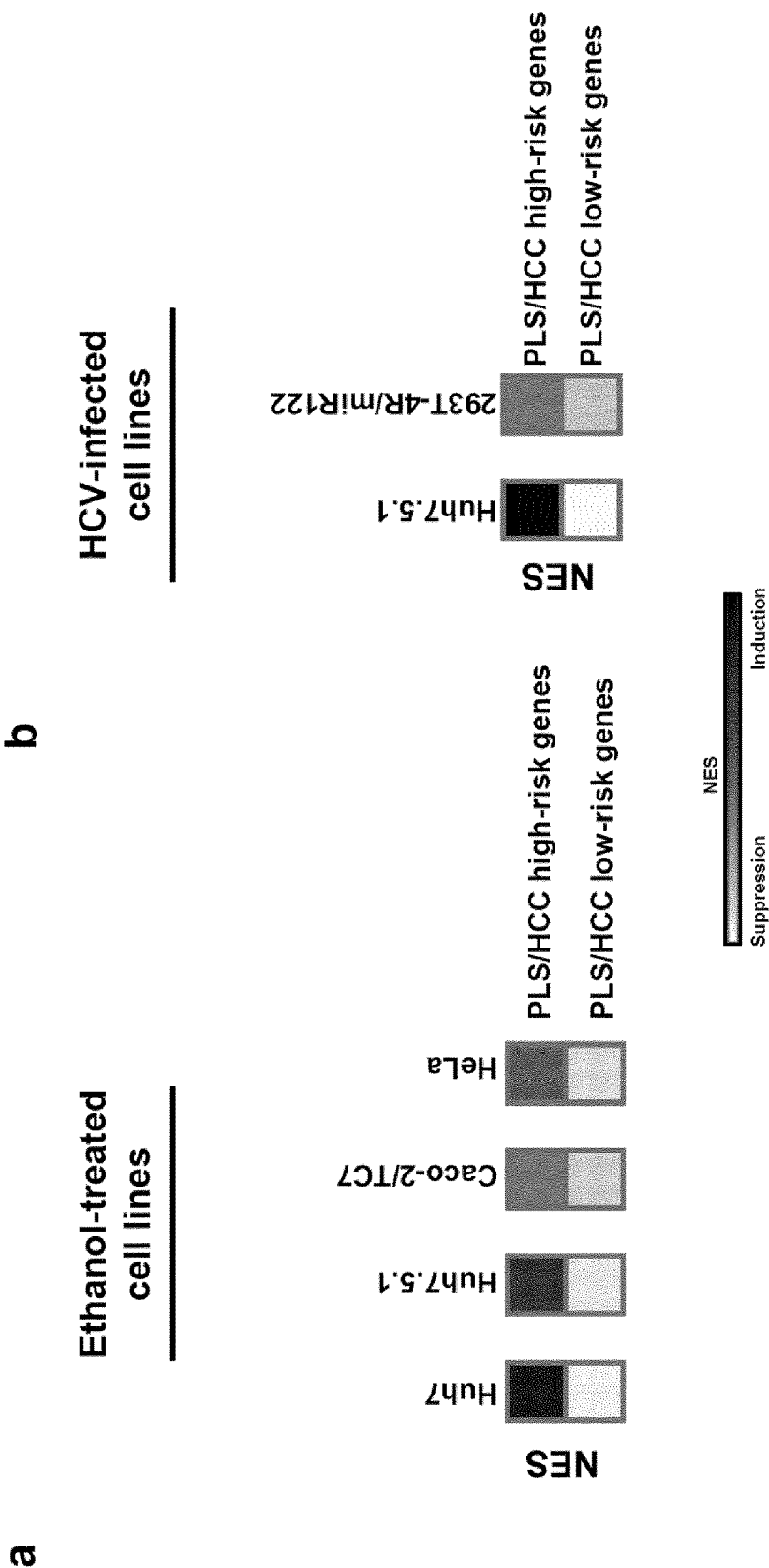
FIG. 9. A patient-derived pan-etiology 32-gene PLS risk signature is inducible in liver and colon cell lines. Huh7, Caco-2/TC7 and HeLa cells were exposed to ethanol (40 mM) for 7 or 10 days. Cells were harvested and RNA was isolated. PLS/HCC-risk signature was assessed using Biomark HD high-throughput RT-PCR technology. A. Heatmap showing the induction/suppression of expression of HCC high- and low-risk genes, respectively, after ethanol treatment. B. Heatmap showing induction of gene expression of the high-risk genes and suppression of low-risk genes in HCV infected and DMSO-differentiated Huh7.5.1 but not in 293T-4R/miR122 cells. In scale bar, white indicates significant suppression, black indicates significant induction. NES: normalized enrichment score.

Transcriptional analyses. Seven days after ethanol exposure or HCV Jc1 infection, cell were lysed using BL/TG buffer and RNA was isolated using ReliaPrep RNA Cell Miniprep System (Promega). Gene expression profiling was performed using 250-500 ng total RNA by using high throughput qRT-PCR Biomark HD (Baker, Nature Meth., 2012, 9: 541-544) or NCOUNTER Digital Analyzer system (NanoString). Induction or suppression of HCC risk signature was determined by Gene Set Enrichment Analysis (GSEA), implemented in GenePattern genomic analysis toolkits Results and Conclusions A patient-derived pan-etiology 32-gene PLS/HCC risk signature is inducible in non-hepatic cancer lines treated with ethanol. To assess whether the 32-gene PLS/HCC risk signature (Table 1b) can also be induced in non-hepatic cell lines, the Applicants assessed the expression of the PLS/HCC-risk genes in colon Caco-2/TC7 and cervix HeLa cells after 7-10 days of ethanol exposure. As positive controls, they used ethanol-exposed Huh7 or Huh7.5.1 cells. Furthermore, they infected an HCV permissive 293T nonhepatic cell line engineered to express HCV host entry and replication factor miR122 cells with HCV. Exposure of colon and cervical cell lines to ethanol resulted in the induction of the expression the HCC high-risk genes and the suppression of the expression of the HCC low-risk genes similar but to a lower extent than hepatic cell lines (FIG. 9A). In contrast to HCV infection of Huh7.5.1 cells resulting in robust and highly significant induction of the PLS/HCC risk signature, HCV infection of the nonhepatic 293T-4R/miR122 cells was less efficient to induce induce the 32-gene HCC risk signature (FIG. 9B). In conclusion, non-hepatic cell lines, including colon (Caco-2/TC7) and cervical (HeLa) cells be used as a model to express the patient-derived pan-etiology 32-gene PLS/HCC risk signature upon exposure to a cancer-inducing agent such as ethanol. In contrast, HCV infection only robustly induces the PLS/HCC risk signature in a hepatic cell line.

Collectively, these results demonstrate that the PLS/HCC signature can be induced upon ethanol exposure in non-hepatic cancer cell lines, suggesting that the treatment of non-hepatic cell lines provide model systems to discover biomarkers and to screen drugs for chronic disease progression, prediction of cancer risk, and cancer development in general.

Example 4: Identification of Serum and Urine Biomarkers for Liver Disease Progression and HCC Risk Prediction Using the Liver Cell Culture Model In the clinical setting, the use of biomarkers requiring liver biopsies hampered by a invasive procedure with risk of complications for the patient. To address the need for a safer and less invasive approach and identify biomarkers, which are secreted into the blood or excreted in the urine, the Applicants studied whether the liver cell model allows to identify secreted proteins which can served as biomarkers to be detected by ELISA in body fluids. To address this question, they selected two proteins of the patient 186-gene HCC signature. These proteins are: FSHB (Follicle-Stimulating Hormone Beta Subunit) and NTS (Neurotensin). Both proteins can be detected in the urine and the serum, respectively. While FSHB has not yet been associated with liver disease, NTS has been shown to play a role in HCC (Tang et al., Hepatology, 2012, 55: 807-820).

Materials and Methods

Cell lines and culture. Huh7.5.1 cells were cultured in Dulbecco's Modified Eagle Medium (DMEM) containing 1% DMSO for differentiation (Huh7.5.1$^{dif}$).

Induction of the PLS/HCC risk signature by persistent HCV infection. Huh7.5.1$^{dif}$ were infected with recombinant HCV Jc1 (genotype 2a/2a; $TCID_{50}$/mL=~$1\times10^6$/mL) or incubated with supernatants from mock-electroporated cells. Supernatants were collected following induction of the PLS/HCC risk signature from day 8-10 post infection.

Detection of secreted proteins as biomarkers using specific-ELISAs. Using ELISA kits, the protein concentrations of FSHB (Clinisciences) and NTS (Clinisciences) were measured according to the manufacturer's instructions.

Results and Conclusions

Figure 10:
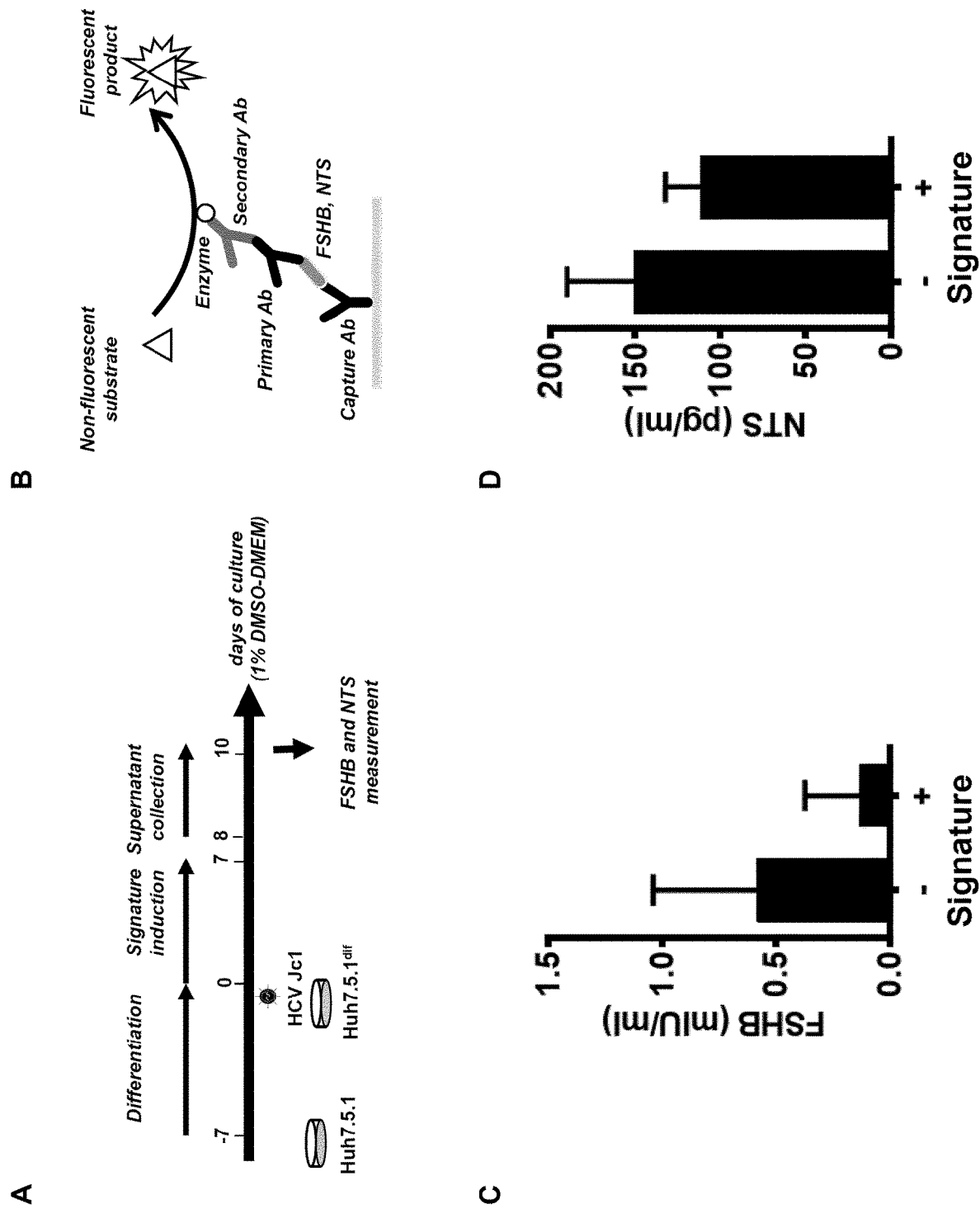
FIG. 10. Detection of serum and urine biomarkers for liver disease progression and HCC risk using the liver cell culture model. The HCC risk signature was induced in A. Experimental Approach: Huh7.5.1$^{dif}$ cells by a 7 day infection with HCV. Following induction of the signature, the medium was changed on day 8 and cell culture supernatant was collected on day 10, reflecting steady-state-levels of secreted proteins within 48 hours. B. Principle of sandwich ELISA for detection of secreted proteins. C. Follicle-Stimulating Hormone Beta Subunit (FSHB). D. Neurotensin (NTS) in the cell culture supernatants were quantified by ELISA.

Detection of candidate biomarkers derived from the patient 186-gene HCC risk signature in the liver cell culture model. To demonstrate that the cell culture model can be used to discover and characterize urine and serum biomarkers, the Applicants analyzed secreted biomarkers in the supernatants of cells with established HCC risk signature. Therefore, Huh7.5.1$^{dif}$ cells were infected with HCV Jc1, and the supernatants were collected from day 8-10 following infection (FIG. 10A). FSHB and NTS proteins were measured in the cell supernatants using protein-specific ELISAs (FIG. 10B). Both proteins were easily detected in cell culture supernatants and their extracellular concentration was different in cells expressing the HCC risk signature or cells with absent risk signature (FIG. 10B C-D).

The results demonstrate proof-of-concept that the cell culture model can be used to identify serum and urine biomarkers for progression of liver disease and prediction of HCC risk.

Example 5: Small Molecule Screen Identifies Epigenetic Inhibitors Targeting Chromatin Remodeling as Candidate Compounds for Cirrhosis/HCC Chemoprevention Liver disease development is accompanied with genetic and epigenetic alterations within liver cells including both hepatocytes and non-parenchymal cells. Epigenome changes have been linked to the development of many diseases, including cancer. Although being heritable, epigenetic modifications are reversible changes that modulate chromatin compaction and gene expression without changing the DNA sequence. While epigenetic changes have been characterized in detailed in established HCC, the role of epigenetic changes in the pathogenesis and progression of virus-induced liver disease prior to establishment of HCC is largely unknown. Here, the Applicants used different liver disease and HCC etiologies, chronic HCV and HBV infection and ethanol exposure as models to investigate and understand the role of epigenetic modifications during liver disease and HCC. Using a liver cell culture system mimicking gene expression in patients with cirrhosis at risk for HCC, they aimed to explore histone-modifying enzymes as targets for pan-etiology HCC/liver cirrhosis chemoprevention and treatment.

Materials and Methods

Cell line and culture. Huh7.5.1 cells (36) were cultured in Dulbecco's Modified Eagle Medium (DMEM) containing 1% DMSO for differentiation (Huh7.5.1$^{dif}$).

Induction of PLS signature by HCV infection and small molecule treatment. For induction of the PLS/HCC risk signature Huh7.5.1$^{dif}$ cells were plated in 6-well plates and infected with recombinant HCV Jc1 (genotype 2a/2a). iBET (0.05 μM), WDR5-0103 (100 μM), SAHA (2.5 μM), C646 (10 μM) and CTK7A (100 μM) were added at day 7 or 9 post-infection. HCV infection was assessed at day 10 by qRT-PCR of intracellular RNA as described (Xiao et al., PLoS pathogens. 2014, 10(5): e1004128).

Induction of PLS signature by HBV infection and small molecule treatment. HepG2-NTCP cells were plated in 12-well plates and infected with recombinant HBV (strain ayw, genotype D) (Ladner et al., Antimicrob Agents Chemother, 1997, 41: 1715-1720) (13). iBET (0.05 μM), WDR5-0103 (100 μM), SAHA (2.5 μM), C646 (10 μM) and CTK7A (100 μM) were added at day 7 post-infection. HBV infection was assessed at day 10 post-infection by qRT-PCR quantification of HBV pregenomic RNA (pgRNA) as described in (Verrier et al., Hepatology, 2015, 63: 35-48).

Induction of PLS signature by ethanol exposure and small molecule treatment. Huh7.5.1$^{dif}$ cells were plated in 12-well plates and exposed to ethanol (40 mM). iBET (0.05 μM), WDR5-0103 (100 μM), SAHA (2.5 μM), C646 (10 μM) and CTK7A (100 μM) were added at day 7 post-infection. Fresh medium containing ethanol and antibodies was replenished daily (Ye et al., Drug Alcohol Depend., 2010, 112: 107-116).

Transcriptional analyses. Ten days after HCV Jc1 and HBV infection or ethanol exposure, cultures were lysed using TRI-reagent (MRC) and RNA purified using the Directzol mini kit (Zymo Research). Gene expression profiling was performed using 250-500 ng total RNA by using either NCOUNTER Digital Analyzer system (NanoString) or high throughput qRT-PCR Biomark HD (Baker, Nature Meth., 2012, 9: 541-544) or NCOUNTER Digital Analyzer system (NanoString). Induction or suppression of HCC risk signature was determined by Gene Set Enrichment Analysis (GSEA), implemented in GenePattern genomic analysis toolkits.

Results and Conclusions

A targeted small molecule screen identifies epigenetic inhibitors targeting chromatin remodeling as candidate compounds for cirrhosis/HCC chemoprevention. Epigenetic drugs may be used as chemopreventive agents by targeting the molecular players of epigenetic reprogramming contributing to HCC. As a model, the Applicants used Huh7.5.1$^{diff}$ cells infected with HCV or exposed to ethanol and HepG2-NTCP cells infected with HBV and studied whether epigenetic inhibitors targeting chromatin remodeling enzymes are able to revert the virus-induced induction of the patient-derived HCC risk signature in liver cells exposed to different liver disease/HCC etiologies. Following induction of the signature in persistently HCV-infected or ethanol exposed Huh7.5.1$^{dif}$ cells or HBV-infected HepG2-NTCP cells, liver cells were treated with iBET, WDR5-0103, SAHA, C646 and CTK7A epigenetic inhibitors (FIG. 11A). As a readout for transcriptional reprogramming, the Applicants chose the 32-PLS/HCC risk signature (Table 1b). iBET and WDR5-010 suppressed PLS/HCC high risk gene expression in infected or Ethanol-treated liver cells. C464 suppressed PLS/HCC high risk genes only in HBV infected cells (FIG. 11b) (Table 4). Taken together, these data suggest that inhibitors of chromatin-remodeling enzymes may be used for cirrhosis/HCC chemoprevention and treatment. Small molecule inhibitors of epigenetic modifications are drugs for prevention and treatment of progression of liver disease and HCC prevention.

TABLE 4

Compounds for prevention and treatment of liver disease and HCC chemoprevention. Candidate compounds reversing the 186- or 32-gene PLS/HCC high and/or low risk genes with FDR values less than 0.25 in liver cells are shown.

| Compounds | FDR-values PLS/HCC suppression of High-risk genes | FDR-values PLS/HCC Induction of low-risk genes |
| --- | --- | --- |
| AM095 | 0.12 | 0.14 |
| Brefeldin-a | 0.2 | 0.025 |
| C646* | 0.21 | 0.8 |
| Captopril* | 0.04 | 0.096 |
| Cediranib | 0.009 | 0.02 |
| CI-1040* | 0.082 | 0.2 |
| Dilazep* | 0.176 | 0.014 |
| Dorzolamide* | 0.043 | 0.1 |
| Erlotinib | 0.2 | 0.4 |
| MK-2206 | 0.01 | 0.06 |
| Nizatidine* | 0.008 | 0.009 |
| Orteronel* | 0.03 | 0.9 |
| PD-0325901 | 0.08 | 0.12 |
| Pimarsertib* | 0.03 | 0.3 |
| Pimozide | 0.09 | 0.09 |
| Pioglitazone* | 0.07 | 0.15 |
| Resveratrol | 0.174 | 0.19 |
| Rolipram* | 0.17 | 0.14 |
| Selumetinib | 0.07 | 0.6 |
| TG-101348* | 0.009 | 0.9 |
| Tivozanib | 0.11 | 0.8 |
| Triamcinolone | 0.017 | 0.08 |
| iBET* | 0.001 | 0.8 |
| WDR5-0103* | 0.19 | 0.5 |

*compounds which have not previously been associated with HCC.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A method for enhancing induction of a Prognostic Liver Signature (PLS) high-risk gene signature in a cellular model for cirrhosis and/or hepatocellular carcinoma (HCC) development and progression, said method comprising steps of:
    (a') differentiating liver cancer cells to obtain hepatocyte-like cells; and
    (b') submitting said hepatocyte-like cells to one hepato-carcinogenic agent to obtain liver cells exhibiting the PLS high-risk gene signature, wherein the hepatocyte-like cells are co-cultured with non-parenchymal liver cells,
    wherein the liver cells exhibiting the PLS high-risk gene signature and obtained in step (b') exhibit:
        an overexpression of at least one gene among 73 high-risk genes, or a subset thereof, that is higher than the overexpression of said at least one gene exhibited by liver cells cultured in the absence of non-parenchymal liver cells, all other things being equal, wherein the 73 high-risk genes are FSHB, SH3GL2, RBM34, NCAPH, EGF, TRIO, COL6A3, ABLIM1, ITGA9, NTS, SERPINB2, MMP7, PRKG2, EDG4, NOS2A, EPHA4, SP100, FMO1, GPX2, ATP4B, IER3, WIPF1, IGFBP6, CTNND2, FBN1, GBA, ICK, CHERP, HDAC9, NOL7, IQGAP1, ADD3, ANXA3, HMG20B, SLC12A2, COL4A1, CPA3, KRT7, SERPINB8, NFKB2, AEBP1, TGFB1I1, EMP2, BCL2, PSMB9, ACTR2, DDR1, SLC7A1, PODXL, COL16A1, IFI30, EPM2A1P1, ANXA1, CCL21, CHSY1, AP1B1, TEAD4, ELOVL2, TCF4, TSC22D2, DUSP5, CCDCl$_6$, CD48, TNK2, DAB2, LOXL2, RNASE1, LPP, CXCR4, SLIT3, FILIP1L, CCL19, and AKAP13, and
        an under-expression of at least one gene of the 113 low-risk genes, or a subset thereof, that is higher than the under-expression of said at least one gene exhibited by liver cells cultured in the absence of non-parenchymal liver cells, all other things being equal, wherein the 113 low-risk genes are ALDH9A1, TTR, RLF, IMPA1, PFKFB1, ACSM3, ADRA2B, PTPN2, PSMB3, PPP1R1A, TMEM97, PKLR, RPS6KA5, CYB5A, SCG5, TXN2, PLG, SC5DL, AR, IGF1, SUCLG1, HAAO, C9, TAF1C, CPOX, XPA, HABP2, GHR, PCK1, AKR1D1, ADH5, AARS, C8B, MGC29506, ATP6AP2, DOCK4, PROS1, ZBTB17, DAD1, TIM M8A, HMGCL, C4BPB, TRAF6, EIF2B1, LIPC, PIGK, WDR23, RFC2, GRM5, SDHC, ERCC5, F9, ANKRD46, ART1, CTBS, SLC37A4, ALAS1, VPS41, GCGR, CCT8, BRP44, GRK4, HSPE1, NARS2, DST, ATP2C1, AKR1A1, EMD, CALCR, DLGAP4, RRM1, NENF, SNX10, PMM1, TDO2, GSTM1, SREBF2, PTPN18, ASAHL, PLCG2, KCNJ3, PCYT2, GJB1, TM7SF2, SELENBP1, AOX1, ZER1, ADH6, MSH6, SLC4A4, USP14, C5, RAD52, FAM129A, BAIAP2, SSFA2, PON3, GCKR, CREB1, CUTL2, SFRS2, HMGCR, GGCX, CYP2B6, ZNF185, ARF4, ACOT2, ATP5D, CPN1, PLCB3, INSM1, POLRMT, and HRASLS3.

2. The method according to claim 1, wherein said liver cancer cells are primary cells isolated from a liver cancer tissue sample or cells from a liver cancer cell line.

3. The method according to claim 2, wherein the liver cancer cell line is selected from the group consisting of the Huh7.5.1, Hep3B.1-7, HepG2, HepG2-NTCP, HepG2AD38, HepG2215, SkHepI, C3A, PLC/PRF/5 and SNU-398 cell lines.

4. The method according to claim 1, wherein differentiating liver cancer cells to obtain hepatocyte-like cells comprises culturing said liver cancer cells in the presence of DMSO.

5. The method according to claim 4, wherein said liver cancer cells are cultured in the presence of 1% DMSO in the culture medium (vol:vol) for 7 to 10 days.

6. The method according to claim 1, wherein in step (b'), submitting said hepatocyte-like cells to one hepatocarcinogenic agent comprises submitting said hepatocyte-like cells to one of:
persistent HCV infection,
persistent HBV infection, and
ethanol exposure.

7. The method according to claim 6, wherein persistent HCV infection is carried out for at least 3 days and less than 60 days and wherein persistent HBV infection is carried out for at least 2 days and less than 15 days.

8. The method according to claim 6, wherein ethanol exposure is carried out in the presence of between 20 mM and 60 mM of ethanol for at least 1 day, but less than 14 days.

9. A cellular model for cirrhosis/HCC development and progression obtained by a method according to claim 1, wherein said cellular model consists of a heterogeneous population of liver cells consisting of liver cells exhibiting the PLS high-risk gene signature and non-parenchymal cells.

10. The cellular model according to claim 9, wherein the liver cells exhibiting the PLS high-risk gene signature and the non-parenchymal cells are present in a ratio from about 50:50 to about 98:2.

11. A screening method for identifying an agent for the treatment or prevention of cirrhosis/HCC, said method comprising steps of:
(1) generating a cellular model for cirrhosis/HCC development and progression using a method according to claim 1;
(2) contacting cells of the cellular model with a candidate compound;
(3) determining the effect of the candidate compound on the PLS high-risk gene signature;
(4) identifying the candidate compound as an agent useful for the treatment or prevention of cirrhosis/HCC if the candidate compound suppresses the expression of the 73 high-risk genes, or of a subset thereof, and/or induces the expression of the 113 low-risk genes, or of a subset thereof, wherein the subset of said 73 high-risk genes are the 19 high-risk genes: FSHB, SH3GL2, RBM34, NCAPH, EGF, TRIO, COL6A3, ABLIM1, ITGA9, NTS, SERPINB2, MMP7, PRKG2, EDG4, NOS2A, EPHA4, SP100, FMO1, and GPX2 and wherein the subset of said 113 low-risk genes are the 13 low-risk genes: ALDH9A1, TTR, RLF, IMPA1, PFKFB1, ACSM3, ADRA2B, PTPN2, PSMB3, PPP1R1A, TMEM97, PKLR, and RPS6KA5.

12. The screening method according to claim 11, wherein the candidate compound is pre-selected by in silico drug screening.

13. The method according to claim 1, wherein the non-parenchymal liver cells are selected from the group consisting of Kupffer cells, stellate cells, liver resident macrophages, sinusoidal endothelial cells, immune cells, intrahepatic lymphocytes, biliary cells, and any combination thereof.

14. The method according to claim 1, wherein the liver cells exhibiting the PLS high-risk gene signature and obtained in step (b') exhibit:
an overexpression of at least one gene among a subset of the 73 high-risk genes that is higher than the overexpression of said at least one gene exhibited by liver cells cultured in the absence of non-parenchymal liver cells, all other things being equal, wherein the subset consists of the high-risk genes: GPX2, NTS, COL6A3, ANXA1, COL4A1, LOXL2, PSMB9, PODXL, SLC7A1, SP1, ANXA3, TGFB1I1, EGF, IGFBP6, NCAPH, AEBP1, DAB2, GBA, FBN1, CHSY1, TNK2, SLC12A2, CPA3, IER3, ACTR2, IQGAP1, NOL7, RBM34, NFKB2, COL16A1, AP1B1, IFI3, and ABLIM1, and
an under-expression of at least one gene among a subset of the 113 low-risk genes that is higher than the under-expression of said at least one gene exhibited by liver cells cultured in the absence of non-parenchymal liver cells, wherein the subset consists of the low-risk genes: PLG, GJB1, HMGCR, PPP1R1A, LIPC, SREBF2, C8B, C4BPB, HAAO, CPN1, RLF, CTBS, GCKR, ACOT2, SC5DL, GCGR, CYB5A, PCK1, ADH6, TXN2, RPS6KA5, PON3, AKR1D1, C5, DST, ACSM3, PMM1, ATP5D, TMEM97, ATP2C1, CPOX, ANKRD46, PKLR, BRP44, TM7SF2, F9, PTPN18, IGF1, SUCLG1, SNX1, GSTM1, KCNJ3, HABP2, CALCR, ATP6AP2, IMPA1, PROS1, ALAS1, DLGAP4, and ALDH9A1.

15. A cellular model for cirrhosis/HCC development and progression obtained by a method according to claim 14, wherein said cellular model consists of a heterogeneous population of liver cells consisting of liver cells exhibiting the PLS high-risk gene signature and non-parenchymal cells.

* * * * *